United States Patent [19]

Kelman et al.

[11] Patent Number: 4,602,378
[45] Date of Patent: Jul. 22, 1986

[54] X-RAY TABLE

[75] Inventors: Arnold L. Kelman, Bridgeport, Conn.; John F. Prendergast, Franklin, Wis.; Edward P. Stevens, Brookfield, Wis.; George R. Lang, New Berlin, Wis.

[73] Assignee: General Electric Company, Schenectady, N.Y.

[21] Appl. No.: 582,481

[22] Filed: Feb. 28, 1984

Related U.S. Application Data

[63] Continuation of Ser. No. 409,757, Aug. 19, 1982.

[51] Int. Cl.[4] .......................... A61B 6/00; G03B 41/16
[52] U.S. Cl. ......................................... 378/26; 378/91; 378/181; 378/190; 378/196
[58] Field of Search ............... 378/196, 179, 190, 181, 378/91, 26, 25

[56] References Cited

U.S. PATENT DOCUMENTS

| | | | |
|---|---|---|---|
| 2,245,704 | 6/1941 | Newman | 378/196 |
| 2,259,036 | 10/1941 | Goldfield et al. | 378/190 |
| 2,700,735 | 6/1955 | Kizaur | 378/196 |
| 2,872,584 | 2/1959 | Schiring et al. | 378/190 |
| 2,997,585 | 8/1961 | Schiring | 378/196 |
| 3,013,155 | 12/1961 | Schiring | 378/196 |
| 3,708,664 | 1/1973 | Bock et al. | 378/26 |
| 4,211,927 | 6/1980 | Hellstrom et al. | 378/26 |
| 4,315,156 | 2/1982 | Sell | 378/26 |

Primary Examiner—Craig E. Church
Assistant Examiner—T. N. Grigsby
Attorney, Agent, or Firm—Fuller, House & Hohenfeldt

[57] ABSTRACT

Medical diagnostic X-ray table assembly including an X-ray source and detector. The entire assembly is mounted on a cantilevered horizontal transverse pivot for being raised and lowered or tilted as a unit. The table assembly is mounted eccentrically to the horizontal transverse pivot so the table can clear the floor when tilted to the foot down position, yet the table is low enough to be mounted easily by a patient.

The X-ray source and detector means are each supported by a series of superposed carriages driven by lead screw drives, thereby allowing the source and detector to independently translate transversely, longitudinally, and toward or away from the patient support. The X-ray source is also mounted on a transverse axis for being pivoted. A novel hydraulic mechanism is provided for tilting the table.

The table is versatile, as it can be used for a wide range of radiographic and fluorographic studies and does not require wall mounted or ceiling mounted auxiliary equipment to perform chest X-rays and other procedures not possible with conventional freestanding X-ray tables.

15 Claims, 29 Drawing Figures

X-RAY TABLE

This application is a continuation of application Ser. No. 409,757 filed Aug. 19, 1982.

BACKGROUND OF THE INVENTION

The invention is a medical diagnostic X-ray machine and patient support table for performing fluorographic, radiographic, and linear tomographic studies of various anatomical features.

The usual examination room for radiographic and fluorographic study of a patient contains several pieces of equipment. A patient table is provided for supporting and manipulating the patient. A first bucky is mounted in the table and used with a radiographic X-ray tube hung from the ceiling for radiographic studies. A second bucky is mounted to the wall and used with the same X-ray tube for performing chest X-rays. A second X-ray tube is mounted beneath the table, and a spot film device supported above the table is rigidly mounted with respect to the second tube to keep them aligned. An electronic image intensifier is attached to the spot film device for alignment when needed for fluorographic studies. The spot film device and tube carriage are counterbalanced by movable weights in the table. When linear tomography is to be performed, the ceiling mounted X-ray source and table mounted bucky are temporarily coupled by a mechanical linkage.

This arrangement has several disadvantages. First, there is considerable duplication of parts because X-rays are emitted from two different tubes and intercepted by one of four or more different detection devices independently mounted in three locations. Second, the apparatus must be positioned carefully, as the position of the table with respect to the wall must be appropriate for chest X-rays, the area near the ceiling is obstructed by the ceiling mounted parts, and room must be provided to move away and store equipment not being used for a particular procedure. To shift from one mode of operation to another several pieces of equipment must be moved in and aligned, and often the patient must be moved on the support surface of the table.

Other problems relate to the versatility of the table. The movable counterweights mounted in the table for counterbalancing the table-mounted tube carriage can interfere with examination of the patient, as anatomical features overlying the radiopaque counterweights are obscured.

Another problem relating to known patient tables has been how to keep the table high enough to clear the floor when tilted vertically and yet low enough for a patient to easily mount it from the floor. The prior solutions to this problem—a patient step for mounting the table or longitudinal translation of the table during tilting to clear the floor—have been less than ideal.

Still another problem with the prior assemblies is that the overhead X-ray tube emits more stray radiation than a table-mounted tube would.

The prior art designs have also employed less than optimum human engineering. For one thing, prior assemblies with their excess equipment unduly limit lateral access to the patient, thus complicating resuscitation or other manipulation of the patient. Equipment surrounding the patient also can be frightening. Furthermore, assemblies which move the patient table transversely or longitudinally can be hazardous, as the patient is in close proximity to moving parts.

In short, although prior assemblies have been successfully used for radiographic and fluorographic examinations they have several limitations which, if removed, would improve efficiency and safety while allowing the equipment to be used for a wider range of necessary studies.

SUMMARY OF THE INVENTION

One object of the invention is to eliminate the need for a wall mounted bucky, ceiling mounted X-ray source, and ceiling mounted electronic image intensifier in the examination room. A second object of the invention is to reduce the mechanical interdependence of the respective parts of the assembly, so the X-ray source and detector can be independently positioned, the table can be raised and lowered or pivoted about a transverse axis, and the table can be tilted without simultaneously translating the table surface. Another object of this invention is to provide the source and chosen detector with position encoders which generate signals indicating their respective positions.

Another object of the invention is to enable a wide range of examinations to be conducted without moving the patient about on the patient table and without translating the patient table longitudinally or transversely. Still another object of the invention is to improve lateral access to the patient at all times, even while an examination is in progress. Still another object of the invention is to eliminate the need for counterweights, particularly movable counterweights which interfere with certain studies. Other objects of the invention will become apparent from the description and claims which follow.

The essence of the invention is a freestanding X-ray table assembly in which the necessary X-ray source and detectors are all carried on a single table frame supported by a single base. The X-ray source and detector are independently movable longitudinally, transversely, and toward or away from the patient support to provide a wide range of coverage, magnification, and source to image distances without requiring that the patient or patient table be moved with respect to the source and detector. The X-ray source remains below the table at all times, while the detection means are all supported on a common mounting above the table.

The patient table is preferably cantilevered transversely from the base, and pivots about a horizontal transverse axis which can be raised or lowered to raise or lower the entire assembly as a unit. The transverse pivot is offset longitudinally on the table frame to allow the table to clear the floor without being translated when the table is tilted vertically. A particular advantage of the cantilevered structure is that, as the table is supported by one side, the clinician or technician working with the patient can directly approach the patient from the other side without interference from any mechanical part. Procedures performed on a patient positioned on the table are thus simplified, which is important since patients are catheterized or attached to other equipment during some procedures.

The drives for moving the X-ray source and detector with respect to the table are preferably lead screw drives to provide precise, well defined positioning and to eliminate the need for counterweights to counteract heavy moving elements. If the drive components are properly selected, lead screw drives also provide self locking design.

The table assembly is preferably tilted and elevated by independent hydraulic means. The table can be lowered to a modest height such as about 30 inches for mounting, and can easily be raised to any suitable height once the patient is positioned on it. The tilting drive is also a novel arrangement since it provides selective drive functions independent of the table height. If a counterbalance valve is installed as part of the hydraulic system, the system is uniquely fail-safe.

Finally, a bimodal X-ray source is provided having a lower power setting for fluorographic studies and a high power setting and other modifications for radiographic studies. One X-ray source can replace two sources in prior equipment.

DETAILED DESCRIPTION OF THE INVENTION

Although the disclosure hereof is detailed and exact to enable those skilled in the art to practice the invention, the physical embodiments herein disclosed merely exemplify the invention, which may be embodied in other specific structure. While the best known embodiment has been described, the details may be changed without departing from the invention, which is defined by the claims.

Figure 1:
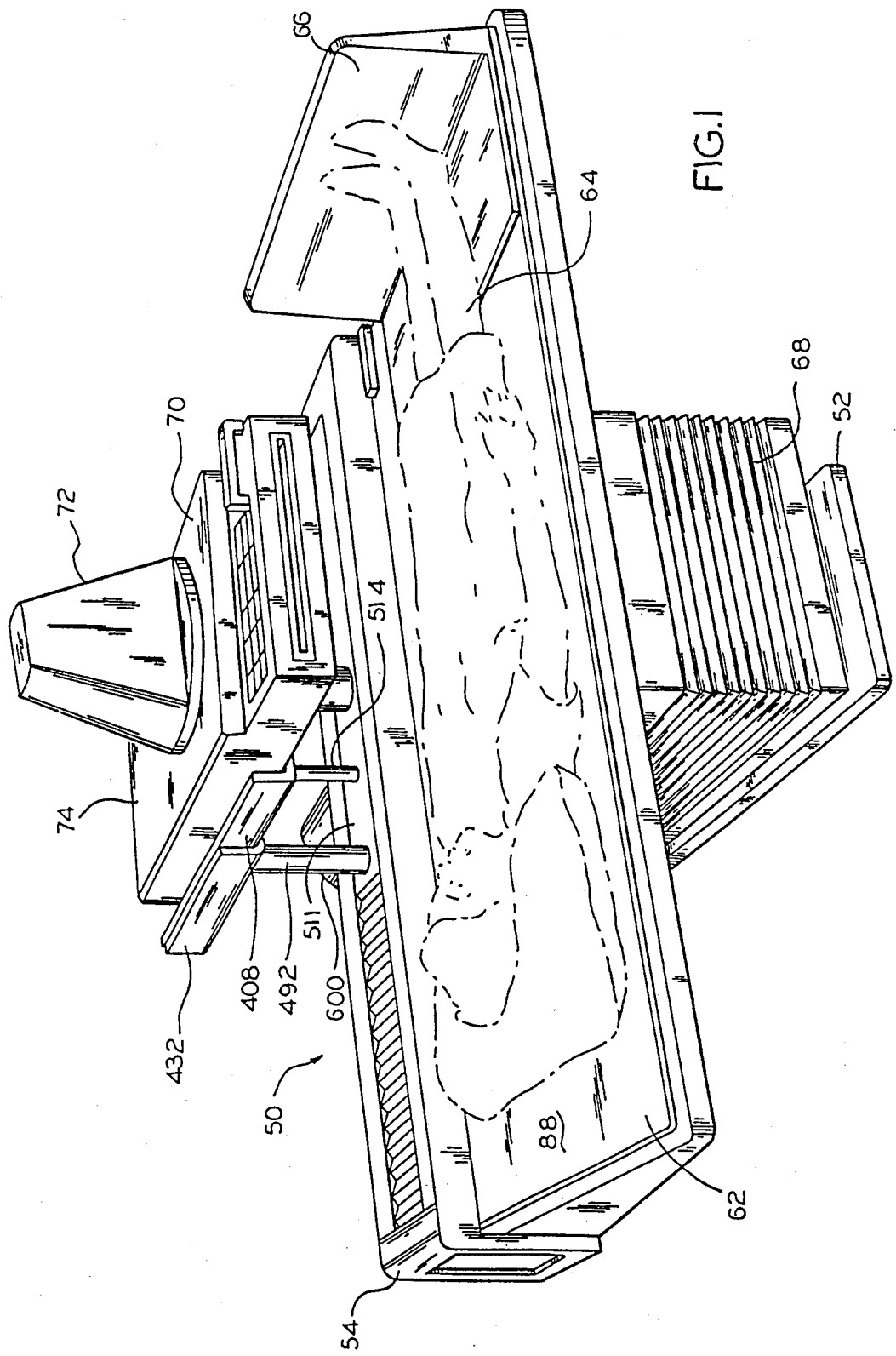
FIG. 1 is a front perspective view of the invention, showing in phantom a patient positioned for examination.
Figure 2:
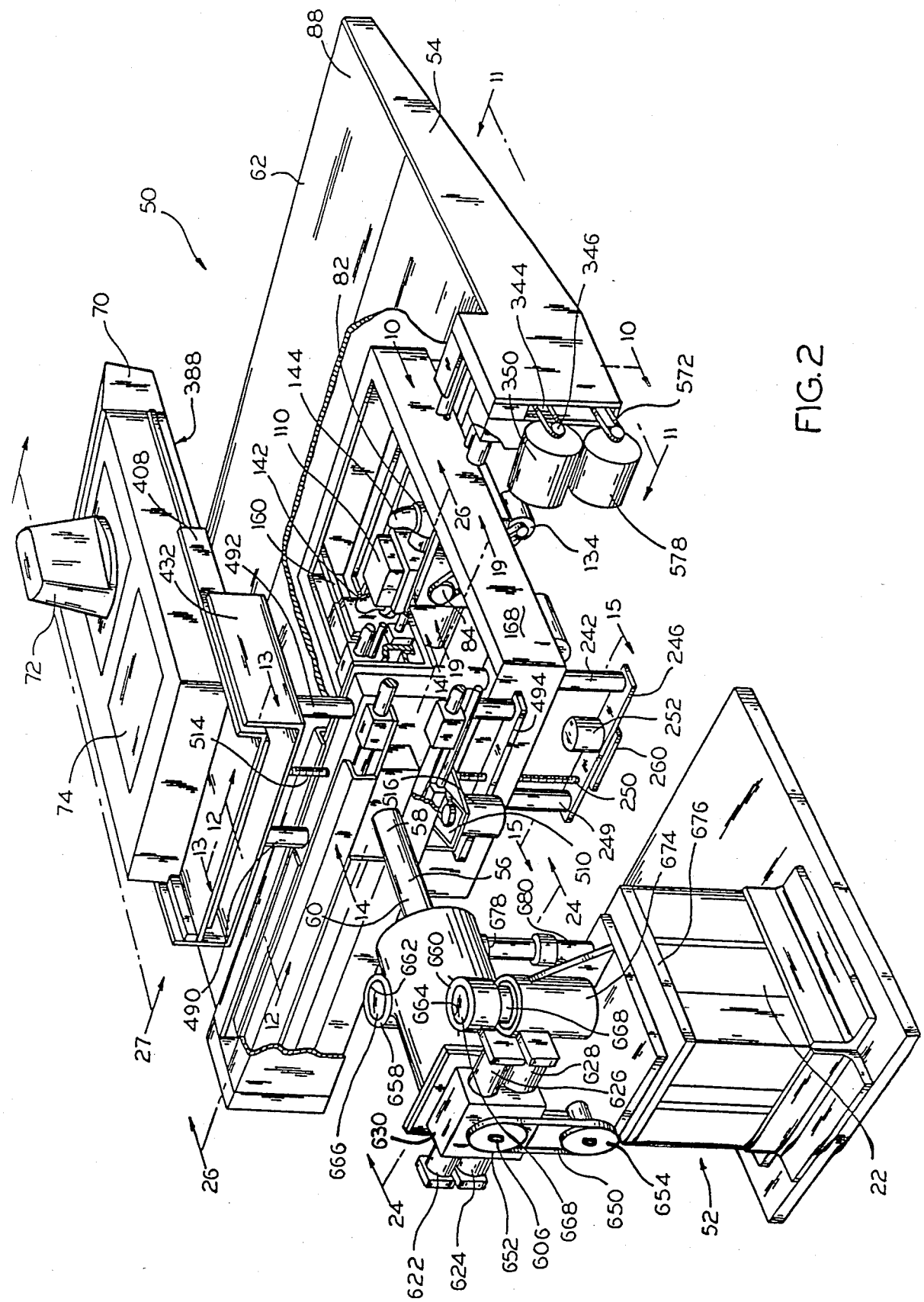
FIG. 2 is a rear perspective view of the invention with several parts broken away to show underlying structures.

FIGS. 1 and 2 show table assembly 50—a complete, freestanding X-ray machine and patient support. Table assembly 50 has a base 52 and a table frame 54 supported by a pivot shaft 56 having one end 58 secured to table frame 54 and its other end 60 secured to base 52, thereby cantilevering table frame 54 considerably beyond base 52. (The exposed length of pivot shaft 56 is exaggerated in FIG. 2 to expose other parts to view.) Table frame 54 can be raised or lowered by raising or lowering pivot shaft 56, and table frame 54 can be pivoted about a transverse horizontal axis by rotating pivot shaft 56. Table frame 54 includes a patient support surface 62 for receiving a patient 64. Surface 62 should be substantially transparent to the radiation of choice. For example, support surface 62 can be made of a composite of graphite fibers in a cured resin matrix, which provides optimal strength and transparency to the X-rays normally used in medical diagnostic machines. A footrest 66 is secured to patient support surface 62 to further support the patient when table frame 54 is tilted.

An X-ray source (within accordion housing 68) and X-ray detector (within housing 70) are located on opposite sides of patient support surface 62, and are provided with means further explained below for transporting them transversely, longitudinally, and toward or away from patient support surface 62. In the illustrated mode of the invention, the X-ray source within housing 68 and the detector housing 70 are provided with independent translation means and drives, thereby eliminating the usual mechanical couplings which limit the motion of the source and detector with respect to each other and to patient support surface 62.

X-ray detector housing 70 supports an electronic image intensifier 72, a spot film device 74, and (referring briefly to FIG. 26) a pair of opposed, parallel guides 76 and 78 constituting an X-ray film cassette holder for locating a film 79 (within film cassette 80) in the path of X-rays emitted by X-ray source 82 within housing 68.

Figure 20:
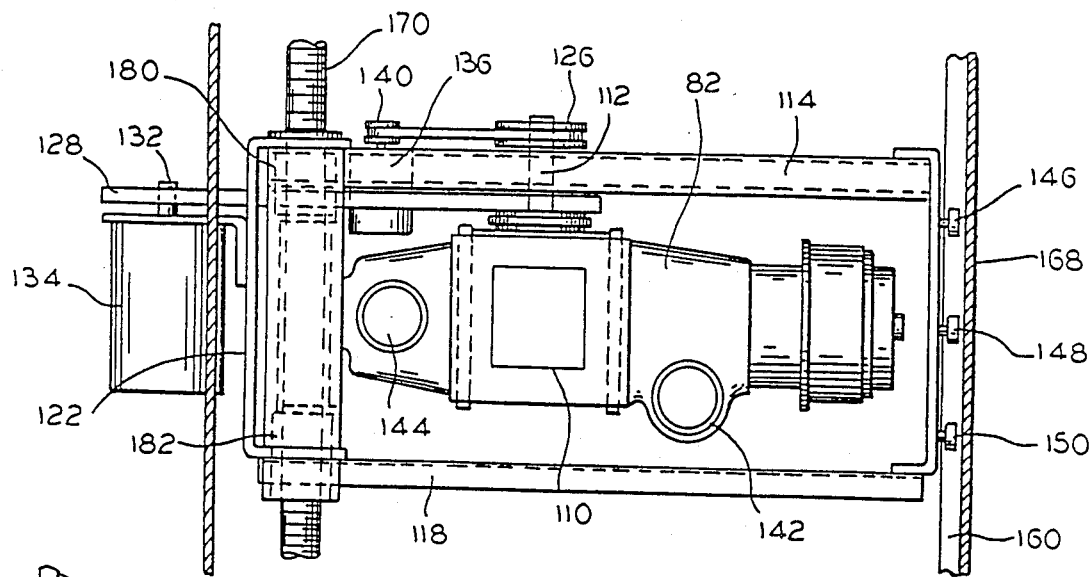
FIG. 20 is a horizontal sectional view taken along line 20—20 of FIG. 19, showing more details of the X-ray source pivoting drive and transverse carriage.
Figure 19:
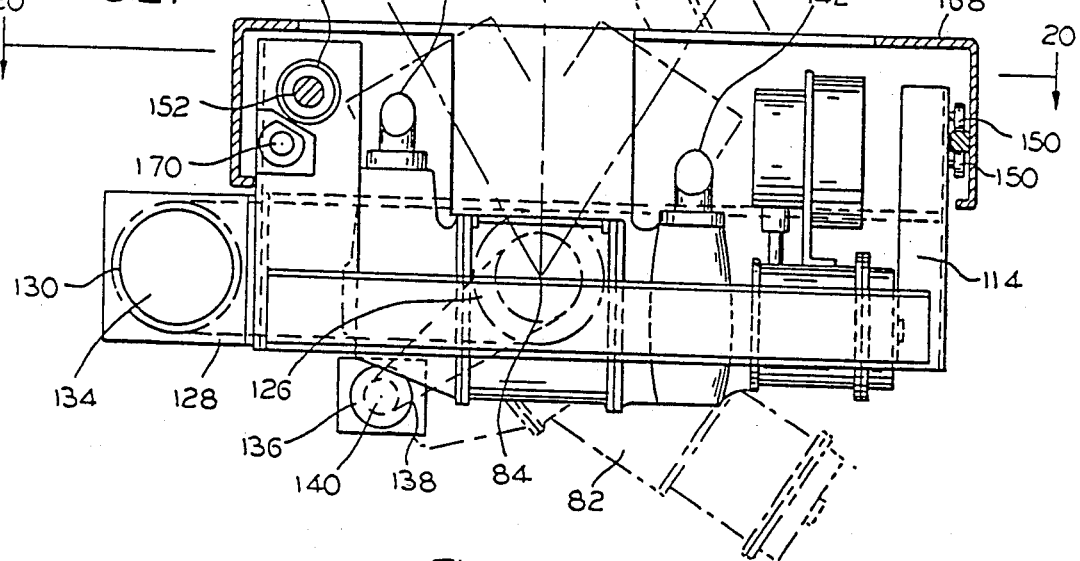
FIG. 19 is a vertical and longitudinal section taken along line 19—19 of FIG. 17, showing the X-ray source pivoting drive secured between the X-ray source and the source transverse carriage.

Referring briefly to FIGS. 19 and 20, an X-ray tube (not shown) is disposed within source 82, which pivots about a horizontal transverse axis 84 parallel to pivot shaft 56.

Referring now to FIGS. 3 through 9, the various operating modes of the table assembly 50 will be further illustrated. The simplified portions of the structure shown in FIGS. 3 through 9 are identified by the same reference characters as the corresponding, more completely shown structural elements in the other figures.

Figure 3:
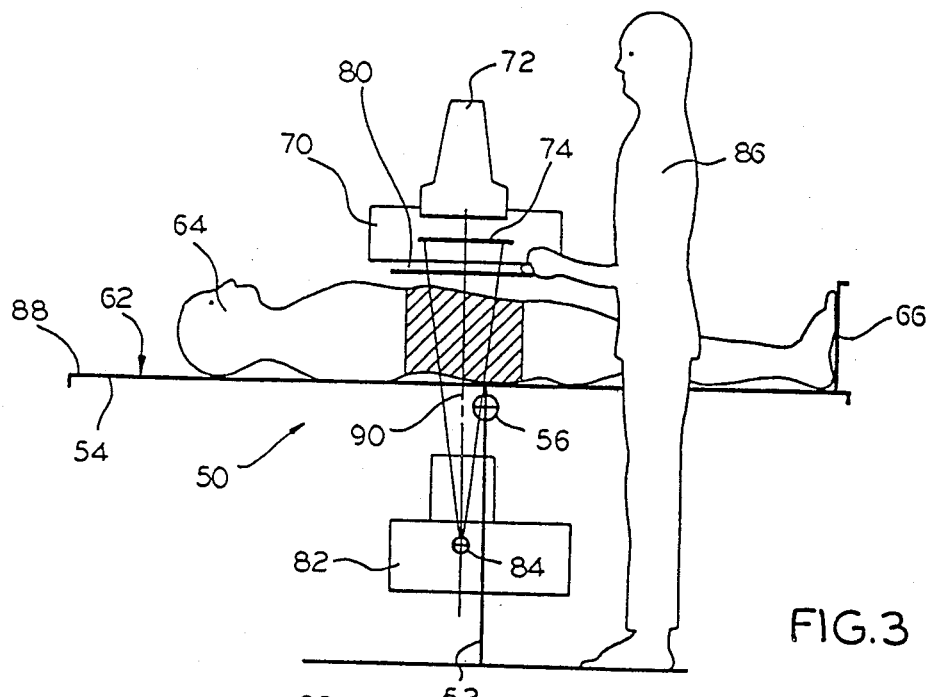
FIG. 3 is a schematic front elevational view of the table, showing the positions of the patient, clinician, and table elements during fluorography performed on a supine patient.

FIG. 3 shows the patient support surface 62 maintained horizontally in its lowest position and the source 82 and detector housing 70 vertically aligned for examining anatomy in the shaded portion of patient 64. This view illustrates that a clinician 86 operating table assembly 50 can operate the table or work on the patient while standing beside patient 64.

Figure 4:
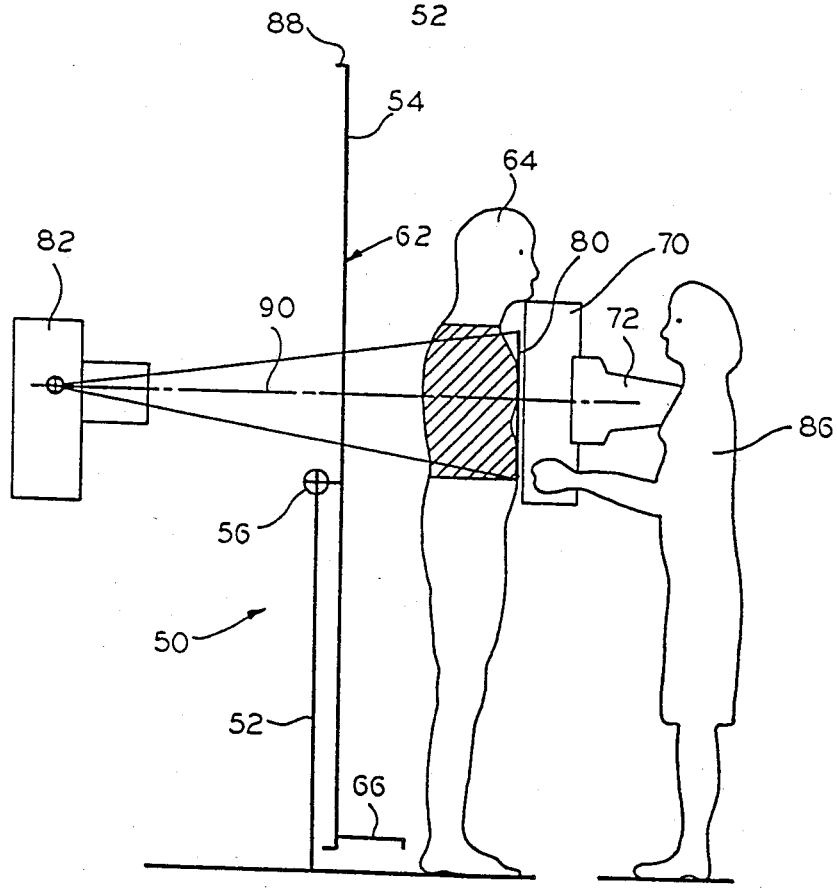
FIG. 4 is a schematic front elevational view of the table, showing the positions of the patient, clinician, and table elements for taking a chest X-ray of an upright patient.

FIG. 4 illustrates an alternate mode of operation in which table frame 54 is tilted about pivot shaft 56 to an upright position. When the machine is so oriented, patient 64 can even step forward of footrest 66 for being positioned directly against film cassette 80 so the distance between X-ray source 82 and patient 64 is increased to provide a view of the entire shaded portion of the patient's anatomy. Again, the clinician or technician 86 is conveniently located for positioning detector housing 70 and operating table assembly 50. Another feature illustrated by FIG. 4 is that the X-ray source housing 68 and detector housing 70 rotate along with table frame 54, thus eliminating the need for a wall mounted bucky to provide chest X-ray capability. Still another feature illustrated by FIG. 4 is that table frame 54 is offset with respect to pivot shaft 56 so the distance between pivot shaft 56 and footrest 66 is less than the distance between pivot shaft 56 and the opposite end 88 of patient support surface 62. This offset allows the table frame 54 to be turned substantially vertically by providing sufficient clearance at footrest 66, even though the pivot axis of the table is lower than was previously necessary. Thus, the need in prior tables for longitudinal translation of patient support 62 while tilting the table frame 54 is eliminated.

Figure 5:
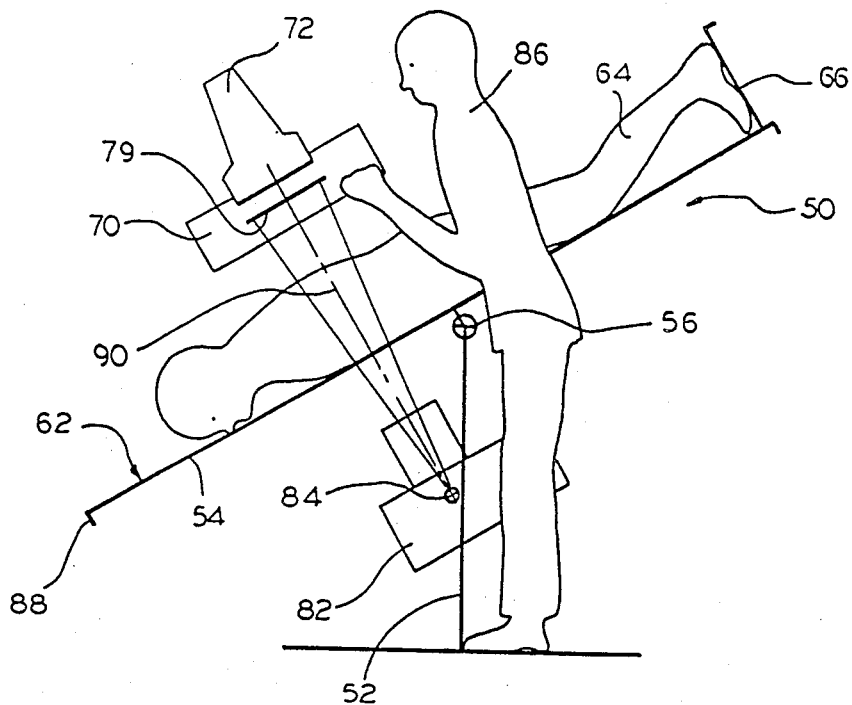
FIG. 5 is a similar view showing the positions of the patient, clinician, and table elements during a particular radiographic study of a patient using a spot film device on a prone patient.

FIG. 5 shows table assembly 50 arranged so that patient support surface 62 is tilted beyond the horizontal position shown in FIG. 3 to a head down position. The X-ray source 82 and detector housing 70 are displaced substantially forward of pivot shaft 56 and so arranged that the central ray 90 of the X-ray beam passes perpendicularly through the patient from back to front while the patient is positioned obliquely with respect to the floor. The clinician or technician 86 again has a convenient place to stand while operating the machinery or working with the patient. FIG. 5 further illustrates that X-ray source 82 and detector housing 70 tilt in coordination with table frame 54.

Figure 6:
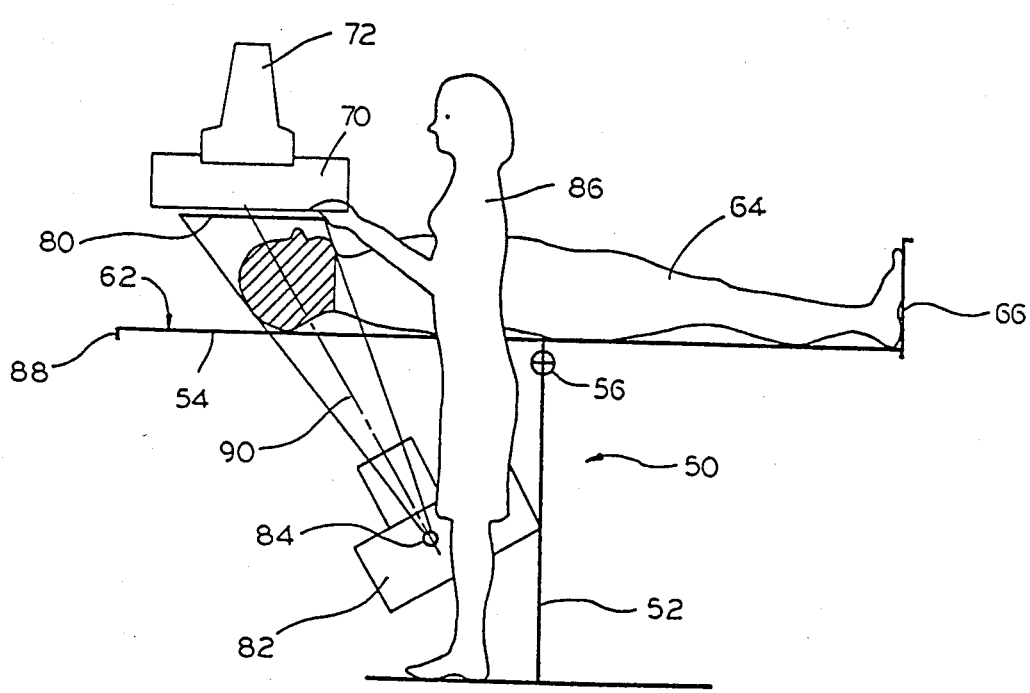
FIG. 6 is a similar view showing the positions of participants and machine elements for oblique radiographic study of a patient's head.

FIG. 6 shows the arrangement of table assembly 50 for oblique radiographic study of the head of patient 64, as illustrated by the shaded portion of the patient's anatomy. X-ray source 82 can be pivoted about its axis 84, which coincides with the focal spot of the X-rays. Source 82 has been shifted further to the left with respect to base 52, while X-ray detector housing 70 has been shifted considerably away from pivot shaft 56 and is positioned in oblique relation to source 82. These respective positions of the source and detector housing would not be feasible if detector housing 70 and X-ray source 82 were relatively immovable or movable only toward or away from each other, as in many prior devices.

Figure 7:
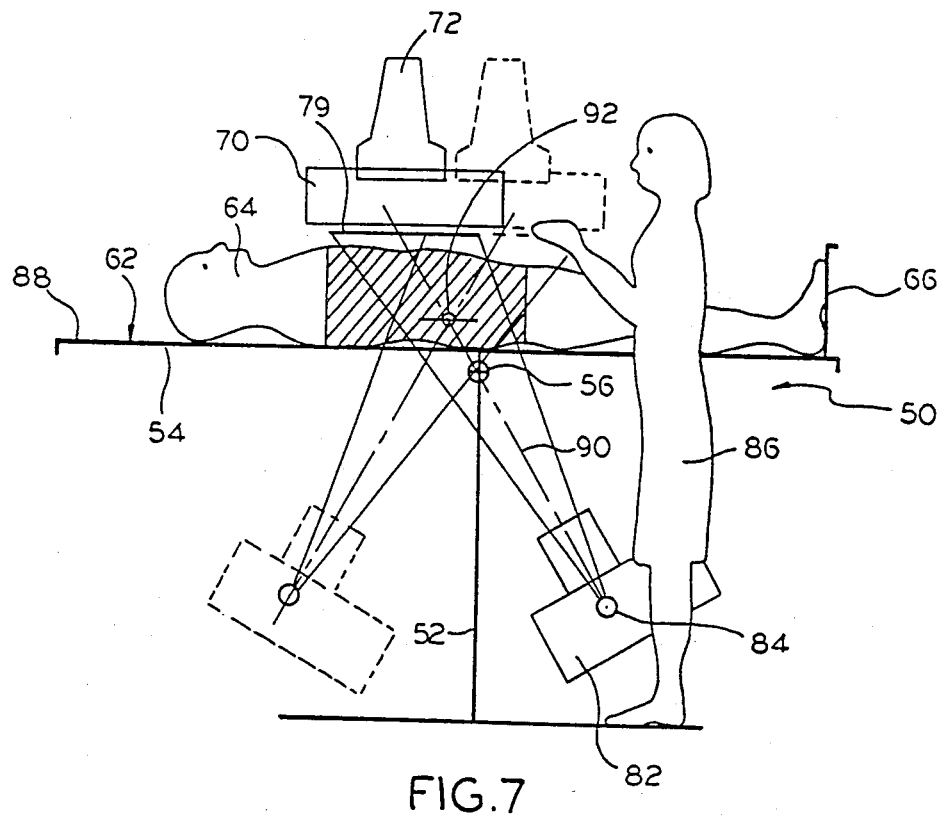
FIG. 7 is a similar view showing coordinated movement of a film holder and X-ray source from the position shown in full lines to the position shown in phantom for performing linear tomography on a patient (who remains stationary during the procedure).

FIG. 7 shows the adaptability of table assembly 50 to linear tomography procedures. The starting positions of X-ray source 82 and detector housing 70 are illustrated in full lines, while their final positions are illustrated in phantom. It will be evident from FIG. 7 that, to keep central ray 90 passing through isocenter 92 and aimed at the appropriate detector (here, film 79) during the procedure, the X-ray source 82 and detector housing 70 must be translated longitudinally in opposite directions and at proportional speeds (the proportion being determined by the respective distances of source 82 and film 79 from isocenter 92). X-ray source 82 is pivoted continuously about its pivot axis 84 to keep source 82 pointed at film 79 during the procedure. As is well known, the purpose of this procedure is to provide a still X-ray image in which the patient anatomy located at isocenter 92 is highlighted on film 79, as the X-rays passing through isocenter 92 are projected onto a single region of film 79.

Figure 8:
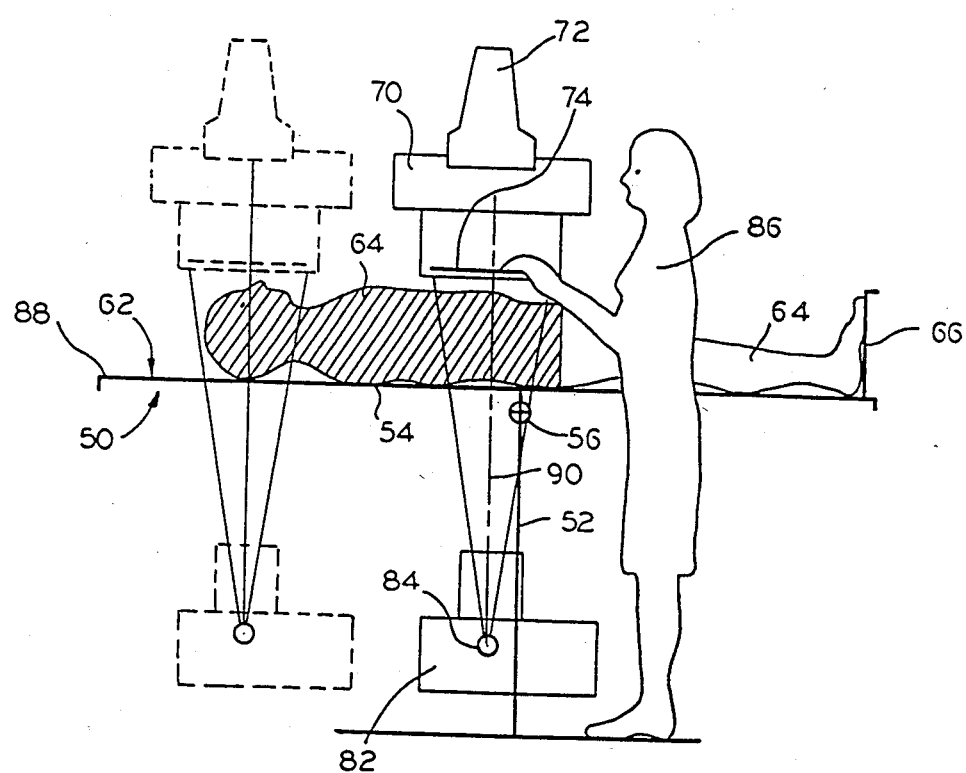
FIG. 8 is a similar view showing coordinated movement of a spot film device and X-ray source from the positions shown in full lines to the positions shown in phantom for preparing longitudinally stepped views of a patient's anatomy.

Turning now to FIG. 8, X-ray table assembly 50 is also capable of taking a series of longitudinally stepped views of the shaded anatomy of patient 64. In this mode of operation the detector housing 70 and X-ray source 82 are indexed simultaneously. Spot film device 74 successively exposes a particular area of the film, advances the film to a new area, exposes that area, and so forth to provide the stepped views. The detector housing 70 and X-ray source 82 are advanced stepwise in synchronization with the operation of the spot film device so the source, detector, and film are stationary while each image is produced by the spot film device. This motion can be preprogrammed to clinically adapt to peripheral vascular recording procedure.

Figure 9:
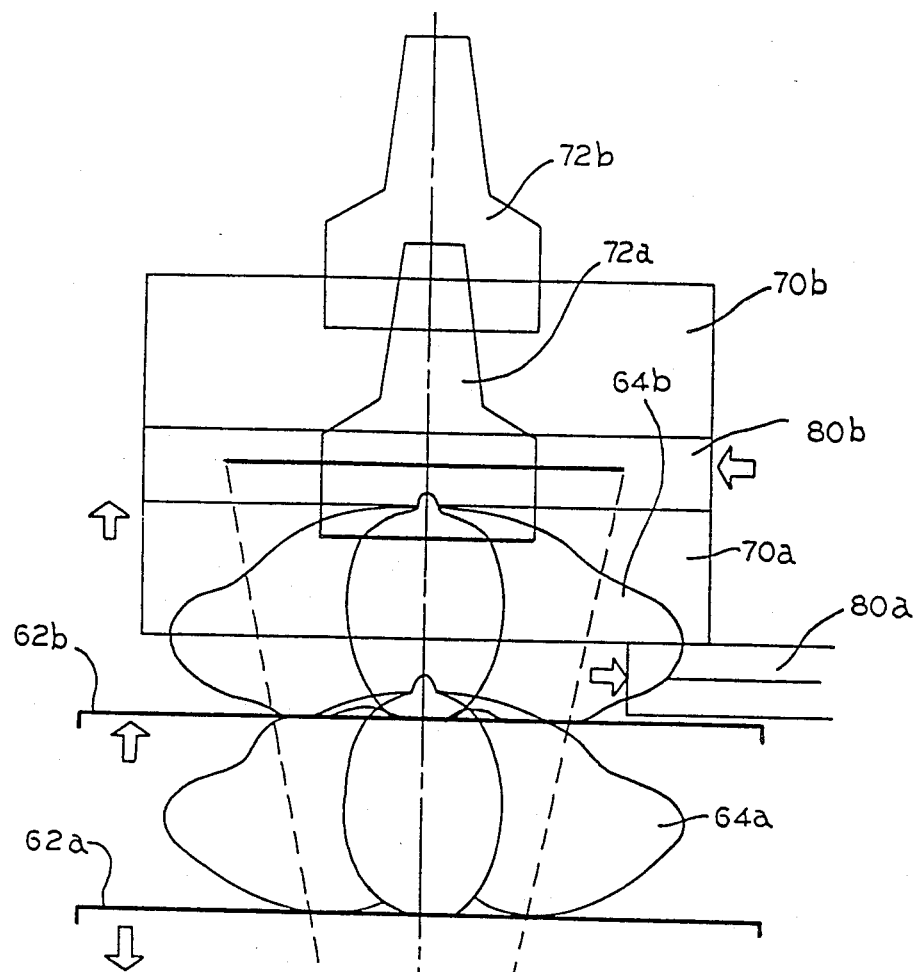
FIG. 9 is a schematic side elevational view of a patient, image intensifier, X-ray source, and patient table according to the present invention, illustrating independent variations in the patient to image distance, the source to image distance, and the height of the table.

FIG. 9 shows that the positions of X-ray source 82, X-ray detector housing 70, and patient support surface 62 can be independently varied, and cassette 80 can be inserted or removed to provide further adaptability of the combination. Assuming for the moment that the table is horizontal (which is not necessarily true in a given situation), each reference character carrying the postscript "a" indicates the lowest position of a structure, while the postscript "b" appended to a reference character indicates the highest position of a structure. Detector housing 70 is thus movable between positions 70a and 70b; film cassette 80 is movable between positions 80a and 80b, position 80a also showing that film cassette 80 can be removed entirely; the position of patient support surface 62 is adjustable between positions 62a and 62b to shift a patient 64 between positions 64a and 64b; and X-ray source 82 can be moved between position 82a and position 82b. Thus, there are a wide range of possibilities for independently changing the source to image distance, the magnification, or the position of the patient.

Although several of the useful features of table assembly 50 have been illustrated in the preceding several figures, these illustrative modes of operation are not intended to be an exhaustive description of all the possible ways of using the machine.

FIGS. 10 through 29 illustrate details of the mechanical arrangement of X-ray table assembly 50.

Referring first to FIGS. 17–21 and 29, X-ray source 82, which emits X-rays through window 110, is mounted on a transversely disposed source pivot shaft 112 coaxial with the focal spot of X-ray source 82. Source pivot shaft 112 is supported by transverse source carriage 114, a rectangular frame comprising longitudinal members 116 (to which source pivot shaft 112 is rotatably secured) and 118 which are joined by transversely extending members 120 and 122. Mounted to pivot shaft 112 are pulley sheaves 124 and 126, the former linked by drive belt 128 to a pulley sheave 130 fixed to the drive shaft 132 of a reversible servomotor 134. Pulley sheave 126, responsive to the rotation of pivot shaft 112, drives an angular position encoder 136 via a drive belt 138 linking sheave 126 to sheave 140. 142 and 144 are the respective conductors which supply electric power to the X-ray tube located within source 82. Motor 134 and encoder 136 are mounted on transverse X-ray source carriage 114.

Transverse source carriage 114 has wheels 146, 148, and 150 rotatably mounted to transverse member 120 and received in a track 160 mounted to one of the transverse members 164 and 166 (here, 164) of vertical source carriage 168. Transverse source carriage 114 thus can travel transversely along vertical source carriage 168. Referring now to FIGS. 17-20, transverse source carriage 114 is located and driven with respect to vertical source carriage 168 by a lead screw 170 received in thrust bearings 172 and 174 mounted to the respective longitudinal members 176 and 178 of vertical source carriage 168. First and second nuts 180 and 182 are fixed with respect to the corresponding corners of transverse source carriage 114 and exert a slight compressive force on the portion of lead screw 170 between them to eliminate backlash (this structure is used throughout, although not always illustrated).

Figure 17:
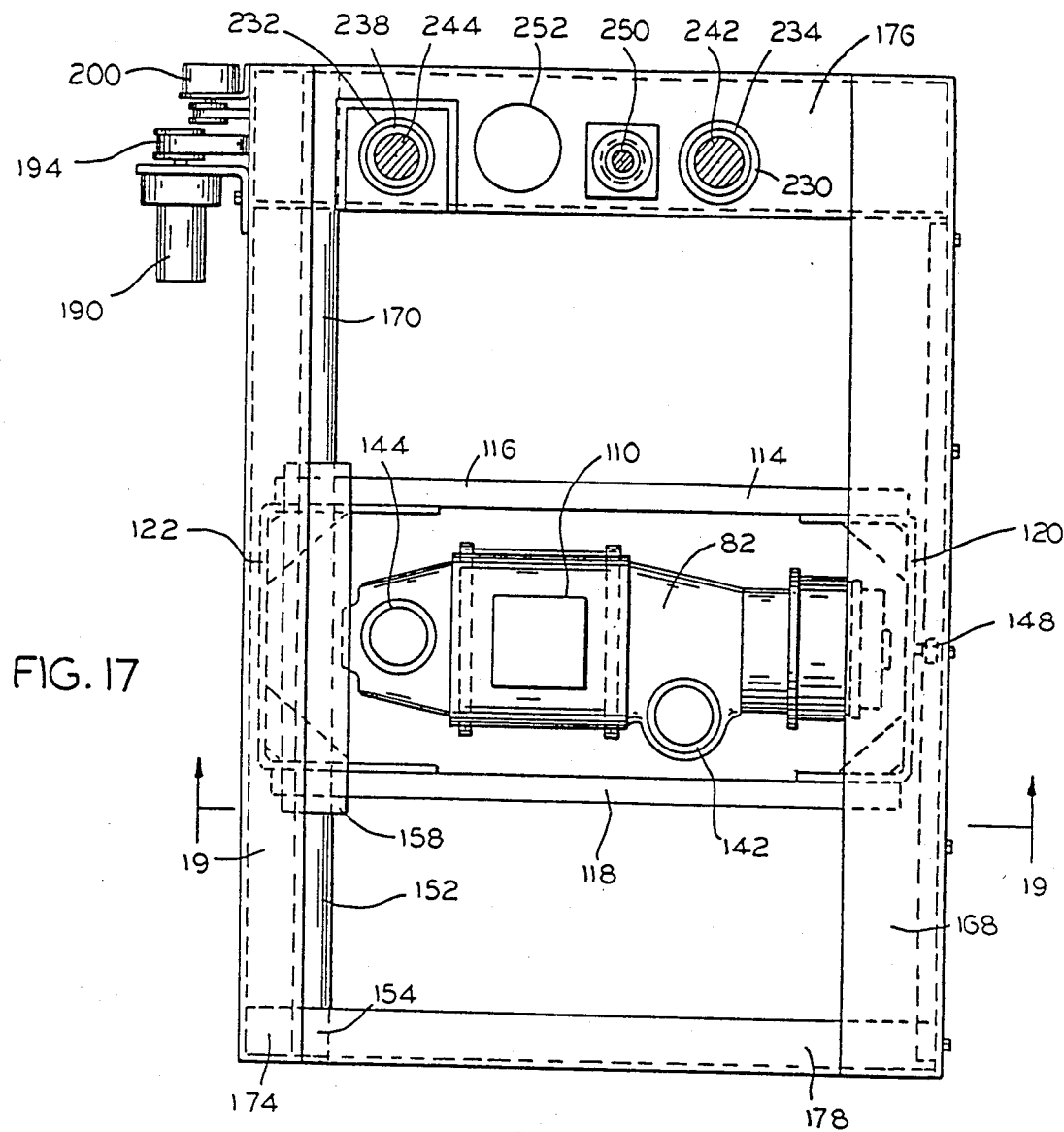
FIG. 17 is a horizontal sectional view taken along line 17—17 of FIG. 15, illustrating the X-ray source pivotally secured to the transverse carriage.
Figure 18:
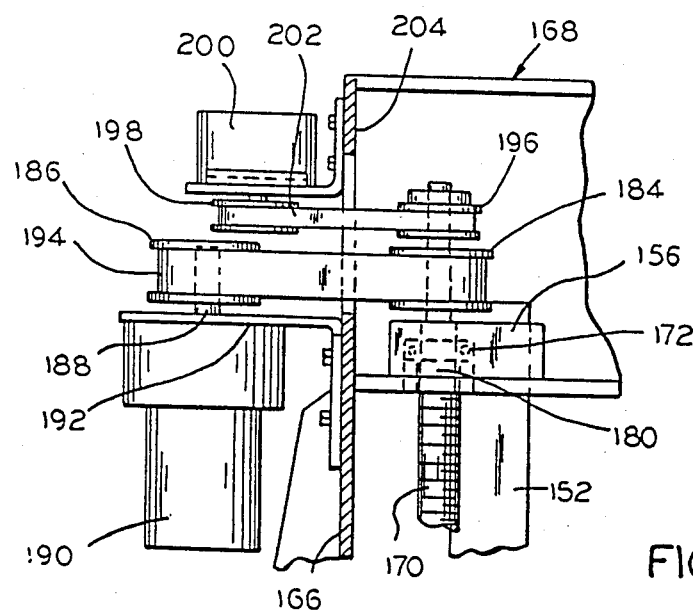
FIG. 18 is an enlarged detail view of the X-ray source transverse carriage drive shown in FIG. 17.

FIGS. 17 and 18 illustrate the drive for lead screw 170, which comprises a sheave 184 keyed to lead screw 170, a sheave 186 secured to the drive shaft 188 of a reversible servomotor 190 fixed by a bracket 192 to transverse member 166, and a drive belt 194 transmitting the rotation of sheave 186 to sheave 184 to drive the lead screw. Another sheave 196 mounted to lead screw 170 drives sheave 198 secured to encoder 200 via belt 202 to transmit to encoder 200 the transverse position of source 82. Position encoder 200 is secured in place by a bracket 204 bolted to transverse member 166.

Figure 21:
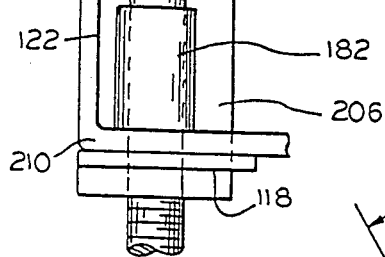
FIG. 21 is an enlarged detail view of FIG. 20, showing the nut secured to the X-ray source transverse carriage and driven by the X-ray source transverse carriage drive.

FIG. 21, a detail view of FIG. 20, shows a strengthening bar 206 to which nuts 180 and 182 are fixedly secured, and which is secured to the inturned end 210 of transverse member 122 and to longitudinal member 118 to form a substantially rigid structure.

Figure 12:
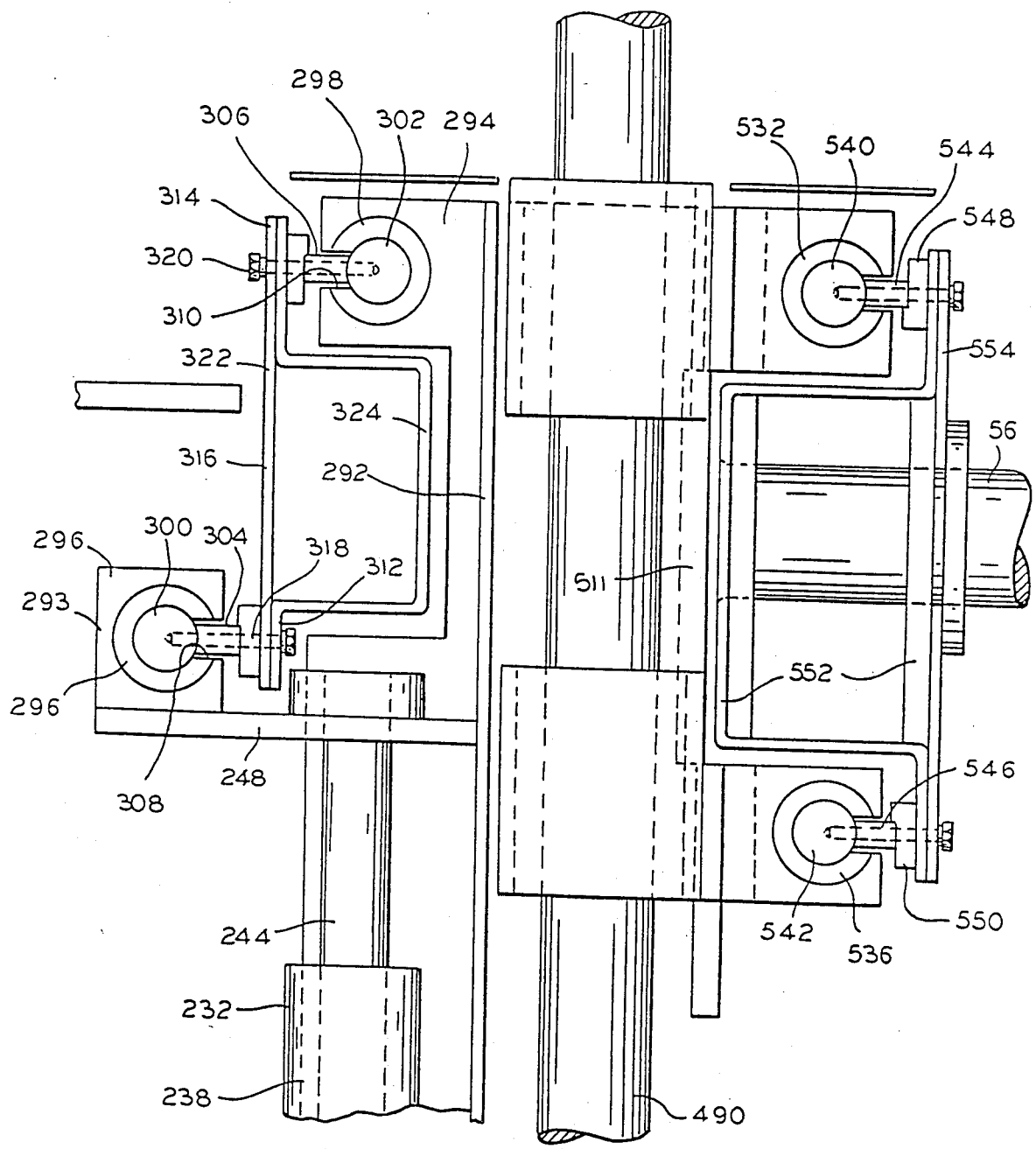
FIG. 12 is a vertical and transverse sectional view taken along line 12—12 in FIG. 2, showing the guides for defining the independent longitudinal and vertical travel of the X-ray source and detector with respect to the table, and also showing the table pivot.
Figure 15:
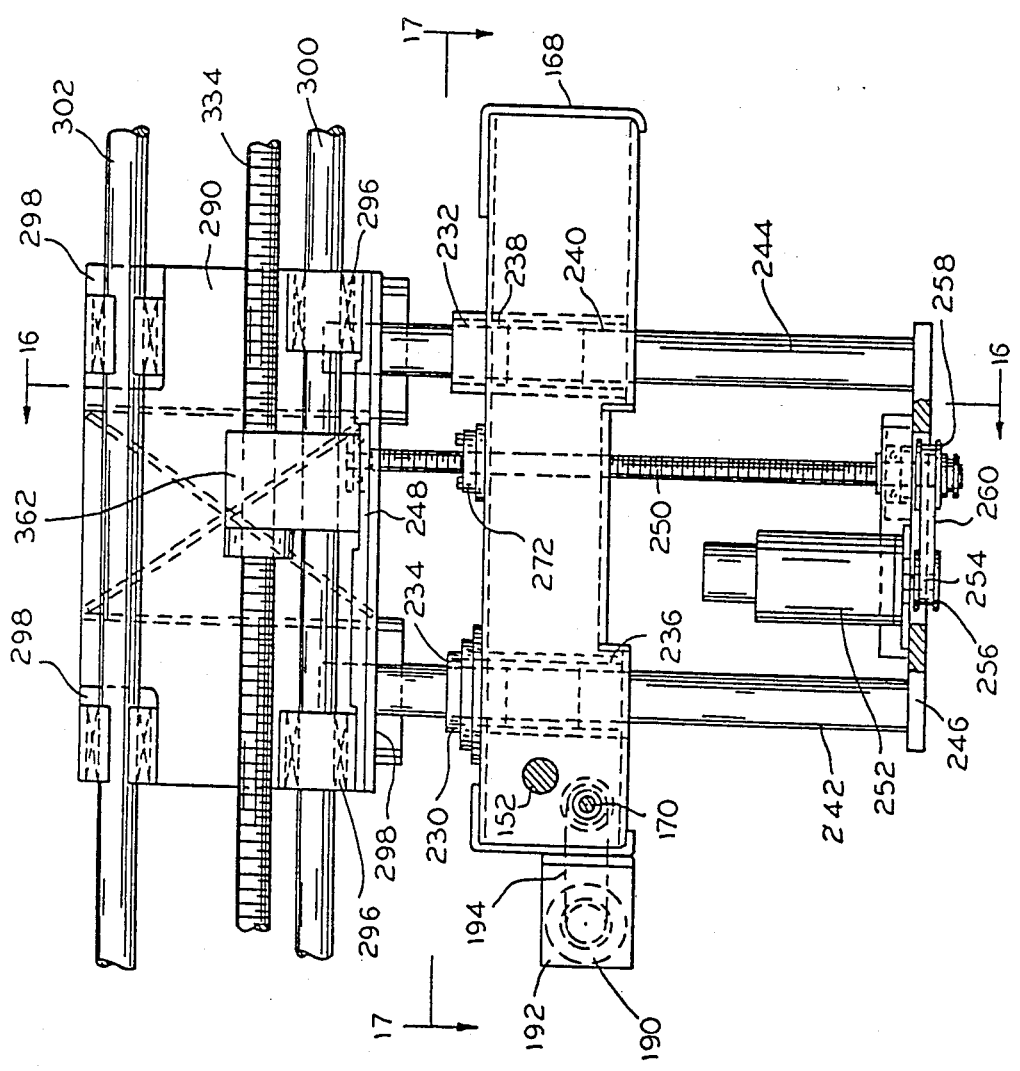
FIG. 15 is a vertical and longitudinal sectional view taken along line 15—15 of FIG. 2, showing the X-ray source vertical carriage and guides, the X-ray source longitudinal carriage and guides, and parts of the drives for moving the transverse carriage, vertical carriage, and longitudinal carriage. The X-ray source is absent from this view.

FIGS. 15, 16, 17, and 29 illustrate the structure for moving vertical source carriage 168 toward or away from patient support surface 62. Sleeves 230 and 232 are fixed to longitudinal member 176 of vertical source carriage 168. Linear bearings 234, 236, 238, and 240 captured within the respective bushings receive vertical guides 242 and 244 which are joined together in parallel relation by plate 246. Vertical guides 242 and 244 are attached, as shown in FIGS. 12 and 15, to a horizontal member 248 which is part of the longitudinal X-ray source carriage 290 described below.

Figure 16:
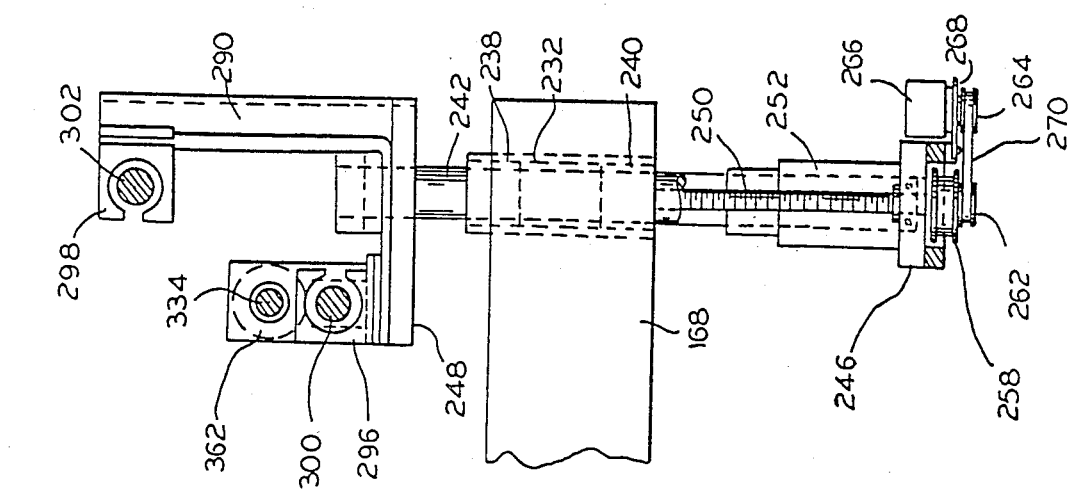
FIG. 16 is a vertical and transverse sectional view of the structure shown in FIG. 15.

To slide vertical source carriage 168 along vertical guides 242 and 244, a lead screw 250 is supported between plate 246 and member 248 by thrust bearings and is driven by reversible vertical source drive servomotor 252. As before, lead screw 250 is connected to servomotor 252 via drive shaft 254, sheaves 256 and 258, and drive belt 260. Referring now to FIG. 16, a sheave 262 secured to lead screw 250 drives the sheave 264 of a position encoder 266 secured by bracket 268 to plate 246; sheaves 262 and 264 are linked in driving relation by a belt 270. Nut assembly 272 secured to a suitable frame member of vertical source carriage 168 is driven by lead screw 250 to move carriage 168 toward or away from patient support surface 62.

Figure 29:
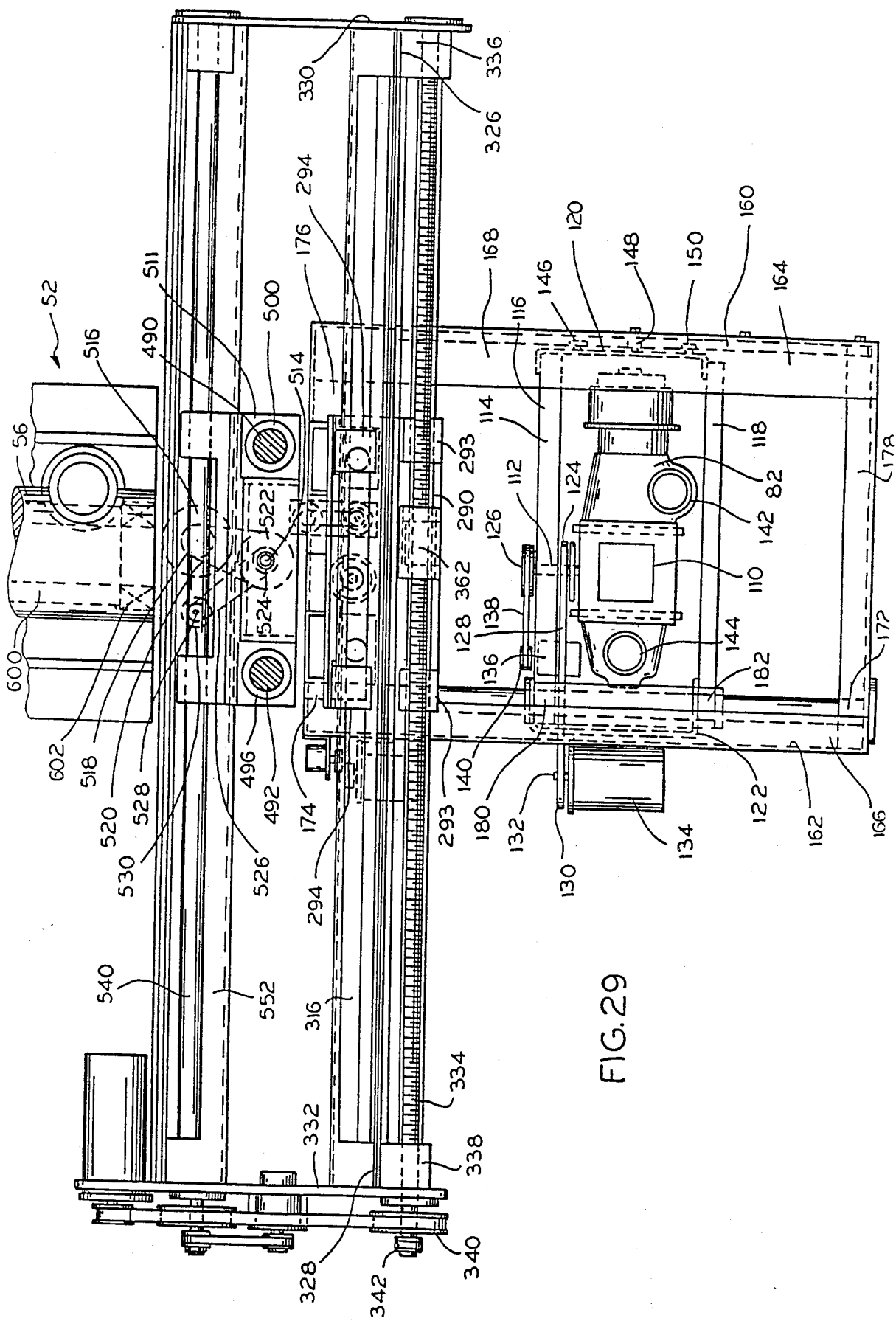
FIG. 29 is a top plan view of the structure of FIG. 2 with the covers and patient support removed.

Referring now to FIGS. 10, 11, 12, 15, 16, and 29, the assembly for moving X-ray source 82 longitudinally can now be described. The longitudinal source carriage 290 comprises the aforementioned member 248 secured to a vertically and longitudinally disposed plate 292. The assembly of members 248 and 292 is stiffened by blocks 293 and 294, which respectively support linear bearings 296 and 298. The latter bearings receive guide rods 300 and 302 disposed longitudinally of the table. Guide rods 300 and 302 are secured by stand-offs 304 and 306 passing through slots 308 and 310 of bearings 296 and 298. Stand-offs 304 and 306 are secured to guide rods 300 and 302 and to the respective ears 312 and 314 of a box beam 316 by fasteners 318 and 320. Box beam 316 comprises a pair of plates 322 and 324 welded or otherwise immovably secured together. Referring particularly to FIG. 29, box beam 316 has first and second ends 326 and 328, respectively attached to transversely extending frame members 330 and 332 of table frame 54. FIG. 29 also illustrates that the entire table frame includes two blocks 293 and two blocks 294.

Figure 10:
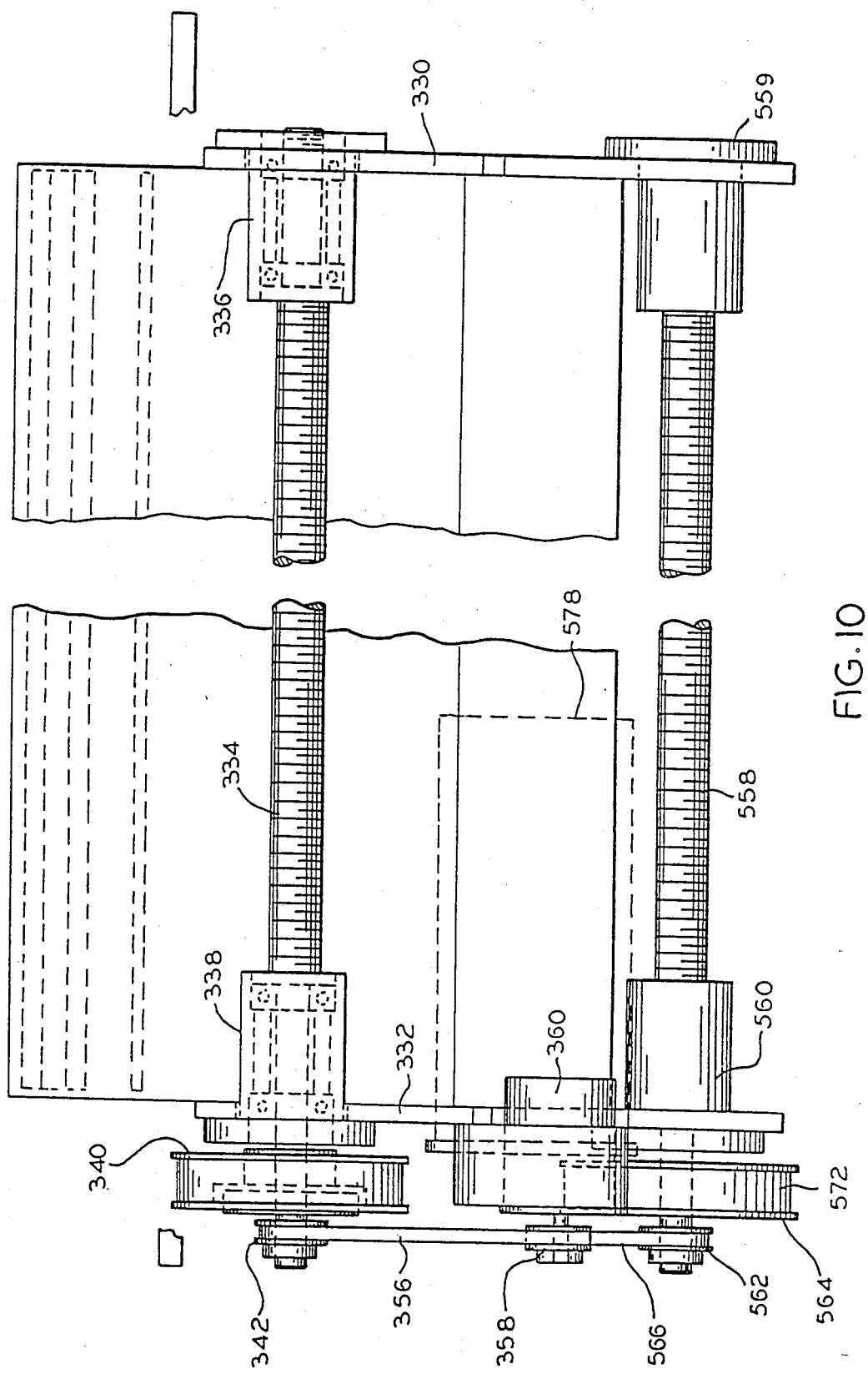
FIG. 10 is a vertical and longitudinal sectional view taken along line 10— in FIG. 2, showing the respective drives and position encoders for independently driving the X-ray source and detector longitudinally of the table.
Figure 11:
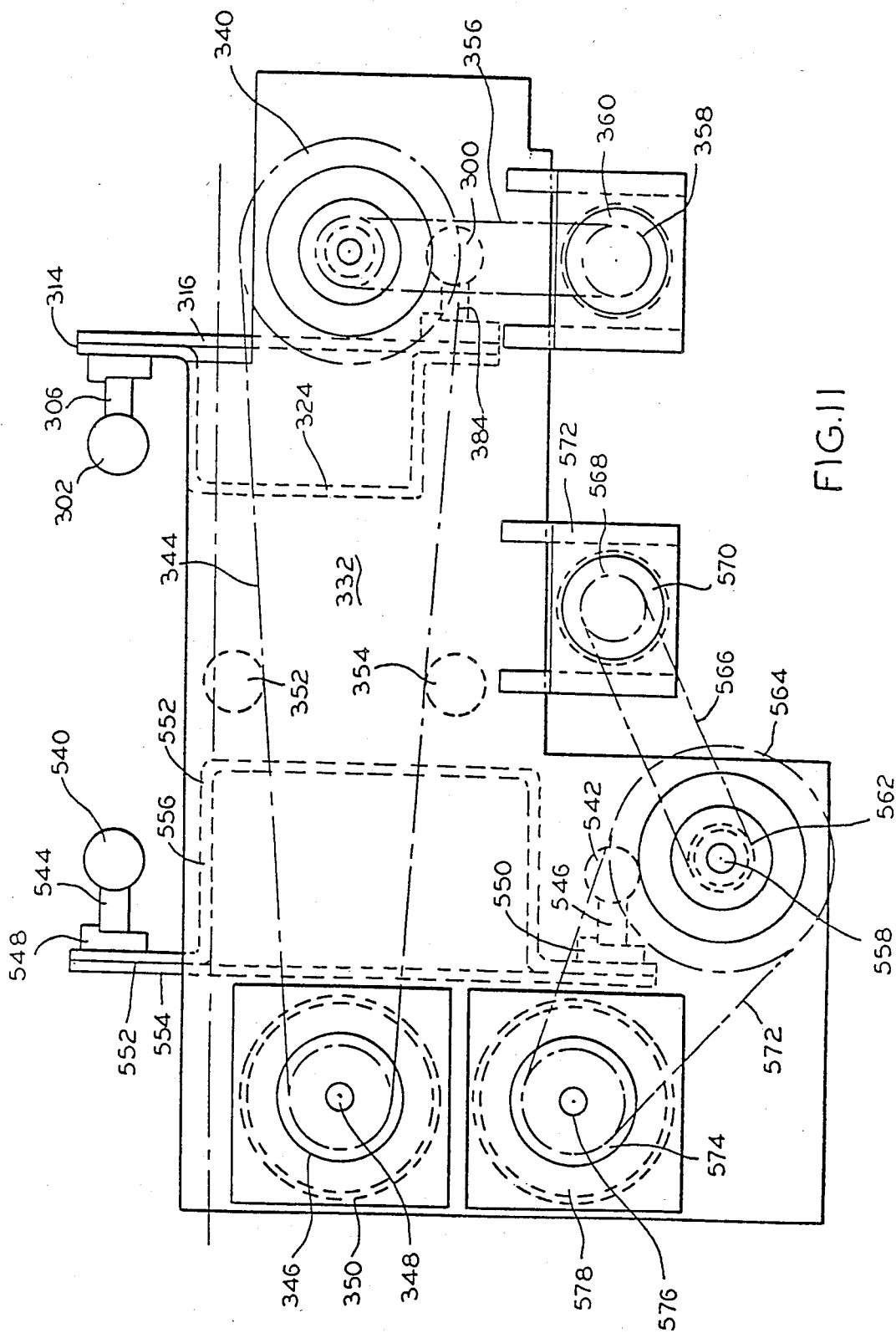
FIG. 11 is a vertical and transverse sectional view taken along line 11—11 in FIG. 2, further showing the structures identified in connection with FIG. 10.

The drive for longitudinal source carriage 290 comprises a lead screw 334 having its respective ends received in thrust bearings 336 and 338 secured to table frame members 330 and 332 for support. Referring in particular to FIGS. 10, 11, and 29, lead screw 334 for the longitudinal source drive has two pulley sheaves, 340 and 342. Sheave 340 is provided to drive lead screw 334 via a drive belt 344 driven by sheave 346 secured to the drive shaft 348 of a reversible servomotor 350. Servomotor 350 is mounted to a stationary element of table frame 54. Due to the length of drive belt 344 in this embodiment, guide pulleys 352 and 354 are pivotally secured to transverse member 332 to maintain the tautness of the belt and to guide it. Sheave 342 drives a drive belt 356, which in turn drives a sheave 358 of encoder 360 to provide an indication of the rotational position of lead screw 334. Referring once again to FIGS. 15 and 29, nut assembly 362 secured to frame member 248 of longitudinal source carriage 290 is threaded on lead screw 334 so rotation of the lead screw drives the longitudinal source carriage 290 along guide rods 300 and 302.

X-ray source 82 thus is moved pivotally about a horizontal transverse axis by operating servomotor 134 and the pivotal position of source 82 is transmitted by encoder 136. Transverse translation of source 82 is effected by operating servomotor 190 and the transverse position of source 82 is transmitted by encoder 200. Source 82 is translated toward or away from patient support surface 62 (vertically, when the table is disposed horizontally) by operating servomotor 252, and its vertical position is transmitted by encoder 266. The longitudinal movement of source 82 is effected by operating servomotor 350 and the longitudinal position of source 82 is transmitted by encoder 360. The position of source 82 at any instant is thus completely defined by the signals transmitted by the encoders. When movement of X-ray source 82 is desired, the signals transmitted by the several position encoders can be analyzed by a microprocessor control unit to determine the initial position of source 82, the necessary translation and pivoting of source 82 can be determined, the several servomotors can be operated to accomplish the necessary movements, and the attainment of the desired final position can be confirmed by using the microprocessor control unit to again analyze the signals sent by the encoders. The microprocessor control can also be used to eliminate the possibility that parts of the table assembly will mechanically interfere with each other or with surrounding objects (such as the floor of the examination room) when table elements are moved. This is done by identifying those simultaneous positions of the table elements which interfere and storing data which characterizes those positions in memory. The microprocessor control can then be programmed to determine whether a proposed change in position will result in interference, and if so to refrain from operating the drives to execute the change in position.

The following description relates to the detector means and their drives and position encoders. First, some consideration of the respective detectors is in order.

Figure 26:
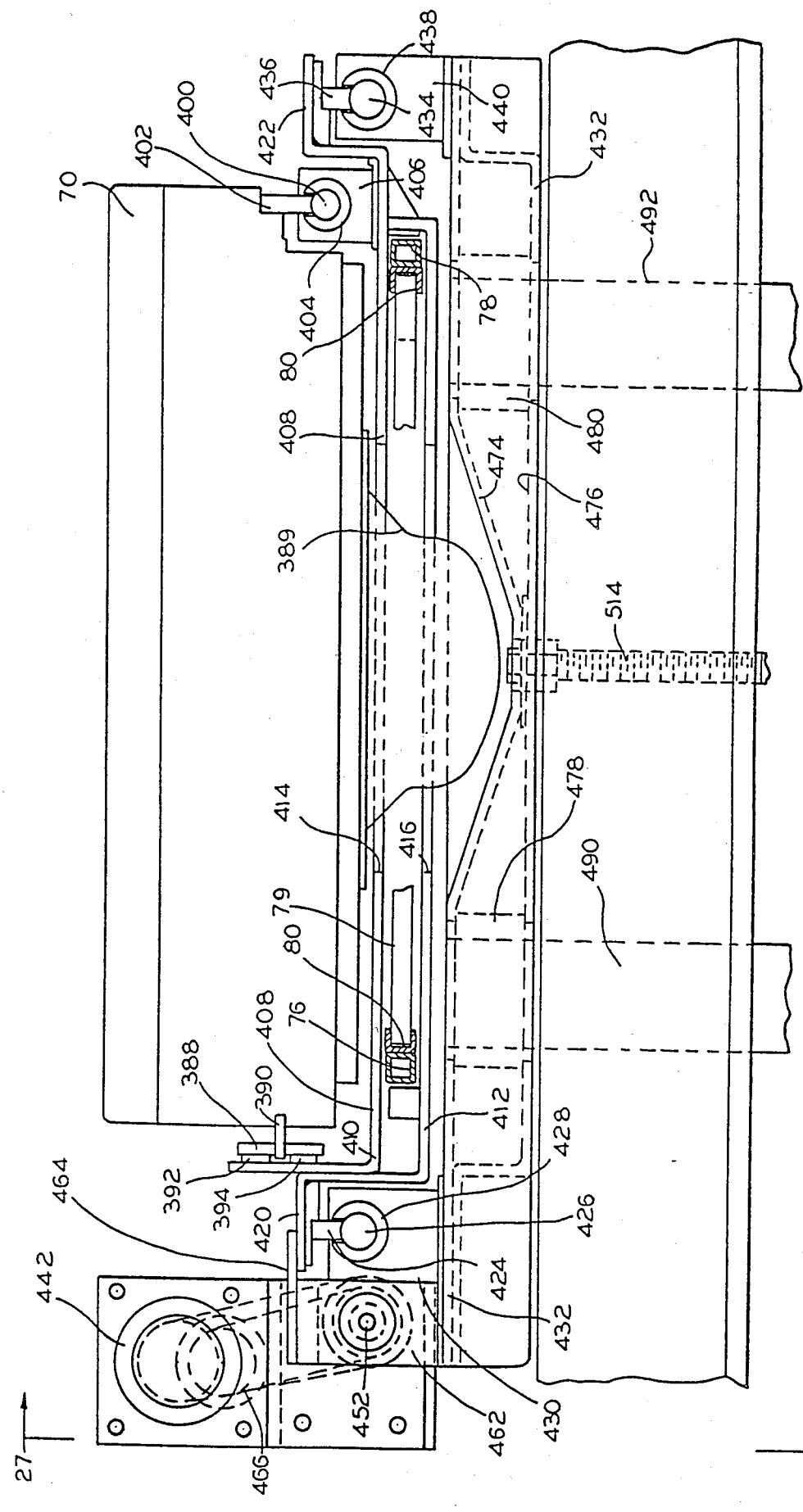
FIG. 26 is a vertical and longitudinal sectional view taken along line 26—26 of FIG. 2, showing the detachable compression cone, film holder, transverse detector carriage drive, and detector parking carriage.
Figure 27:
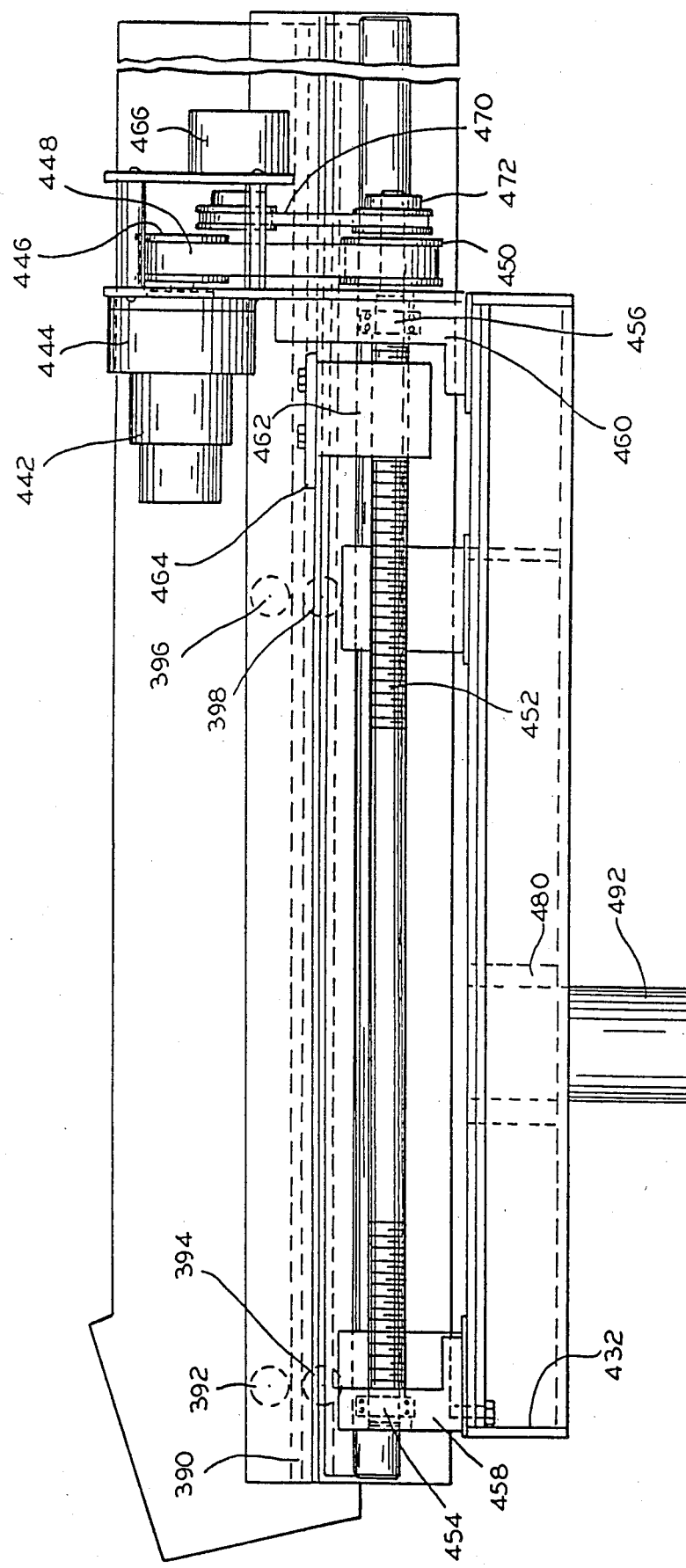
FIG. 27 is a cutaway elevational view similar to a view taken along line 27—27 of FIG. 2, but showing the transverse detector carriage in its parked position.
Figure 28:
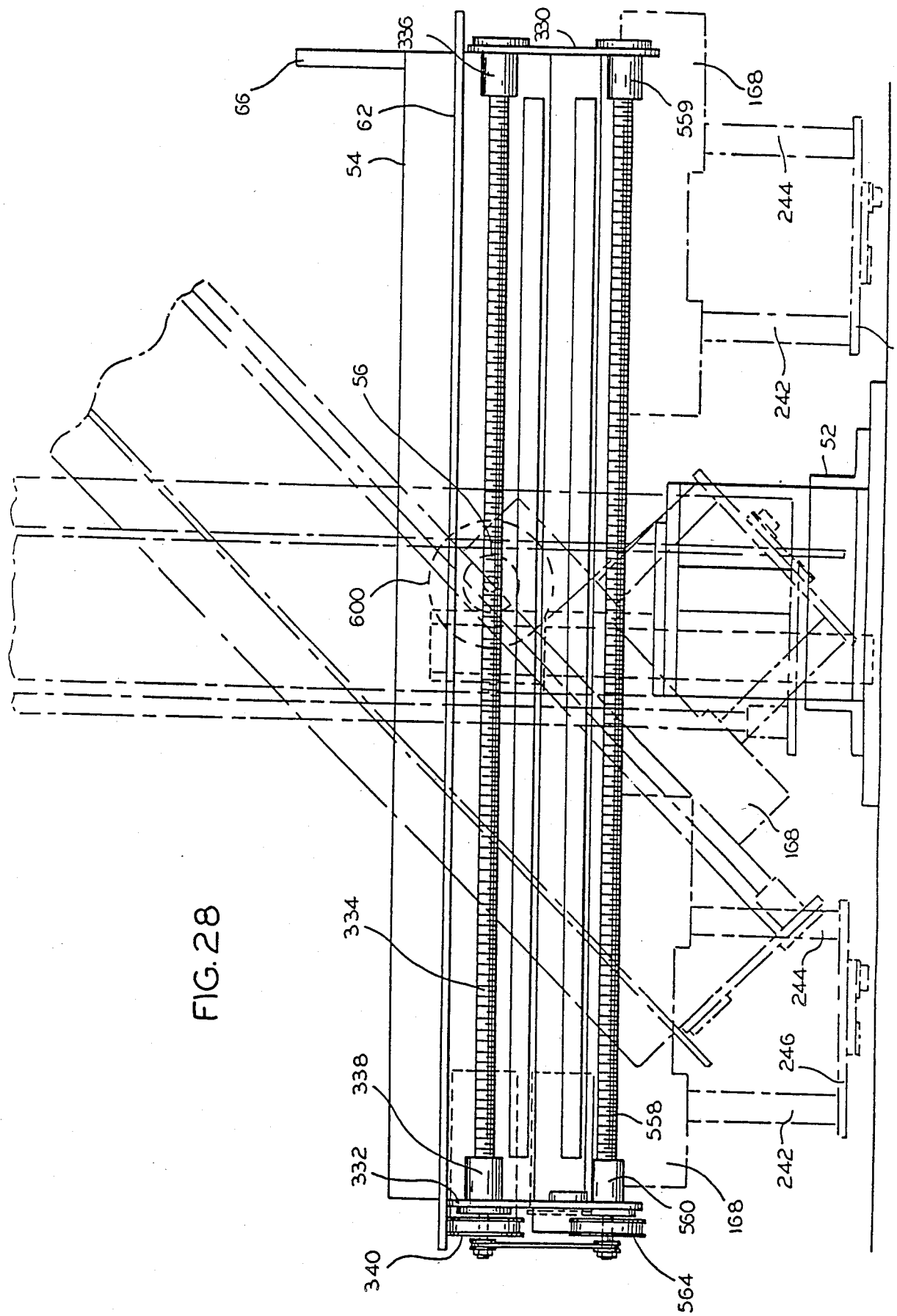
FIG. 28 is a diagramatic view similar to FIG. 1, showing the degree of longitudinal motion of the X-ray source and the effect of tilting the table assembly about its transverse main pivot axis.

Referring to FIGS. 2 and 26, detector housing 70, which supports an image intensifier 72 and spot film device 74, is fixed to a parking carriage 388 to allow housing 70 to be moved transversely between the retracted position shown in FIGS. 26 and 27 and the extended position shown in FIG. 2. The retracted position allows increase access to patient support surface 62, and the extended position is used when image intensifier 72 is spot film device 74 are in use. If a film cassette 80 is to be loaded, it is located by guides 76 and 78 between image intensifier 72 and patient support surface 62 as shown in FIG. 26 (the image intensifier and film cassettes are not used simultaneously). A detachable radiotransparent compression cone 389 can be temporarily mounted to detector housing 70 beneath image intensifier 72 for being pressed against a patient to displace excessive abdominal tissue, providing a film cassette 80 is not then in place.

Parking carriage 388 includes a horizontally disposed slide 390 received between rollers 392, 394, 396, and 398, and further includes a transverse guide rod 400 secured to housing 70 by stand-offs 402 and received in linear bearings 404. Thus, detector housing 70 can be moved transversely between an operating position and a parked position.

Rollers 392, 394, 396, and 398 and a block 406 carrying linear bearings 404 are fixed to a transverse carriage 408 comprising formed plates 410 and 412 welded or otherwise secured together to form a rigid structure. Plates 410 and 412 have apertures 414 and 416 to allow X-rays to penetrate transverse carriage 408 for being received by spot film device 74. For greater structural rigidity, film cassette guides 76 and 78 are secured between plates 410 and 412. Transverse carriage 408 includes horizontally extending, longitudinally spaced ears 420 and 422, the former being secured by stand-off 424 to a guide rod 426 carried in linear bearing sleeve 428, which in turn is fixed to a block 430 secured to the detector vertical carriage 432 (shown in phantom in FIG. 26) to support ear 420 slidably with respect to vertical carriage 432. Similarly, ear 422 of transverse carriage 408 is secured to a guide rod 434 by stand-off 436, guide rod 434 being slidable within linear bearing sleeve 428 secured by block 440 to detector vertical carriage 432 to allow transverse carriage 408 to slide transversely with respect to vertical carriage 432.

Detector transverse carriage 408 is driven by detector transverse servomotor 442 via a gear drive 444 which in turn drives a sheave 446, a drive belt 448, and thereby a sheave 450 secured to a lead screw 452 supported at its respective ends by bearings 454 and 456 secured to brackets 458 and 460 secured to vertical carriage 432. A nut 462 is secured to a plate 464 which is secured to ear 420. Nut 462 is threaded on lead screw 452, thereby allowing reversible servomotor 442 to drive detector transverse carriage 408 transversely. Data indicating the transverse position of carriage 408 is transmitted by an encoder 466 having a sheave 468 driven by a belt 470, in turn driven by sheave 472 secured to lead screw 452.

Figure 13:
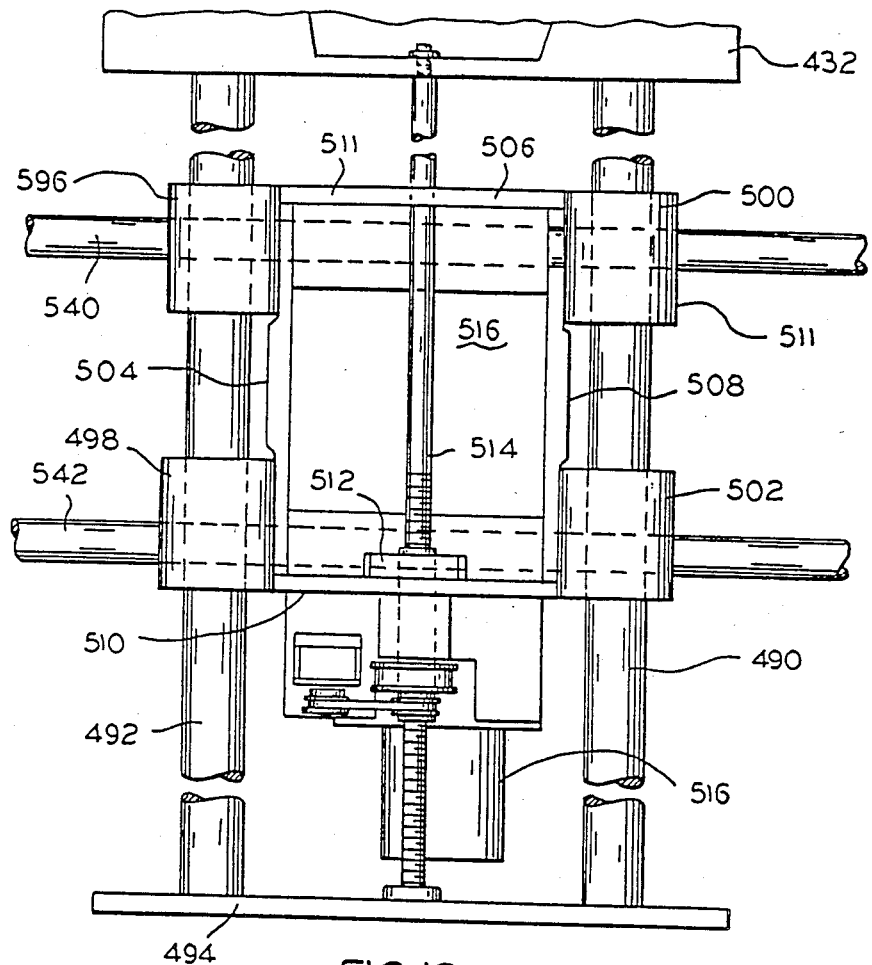
FIG. 13 is a vertical and longitudinal sectional view taken along line 13—13 in FIG. 2, showing the longitudinal carriage, the vertical carriage, and vertical carriage driving mechanism for the detector.
Figure 14:
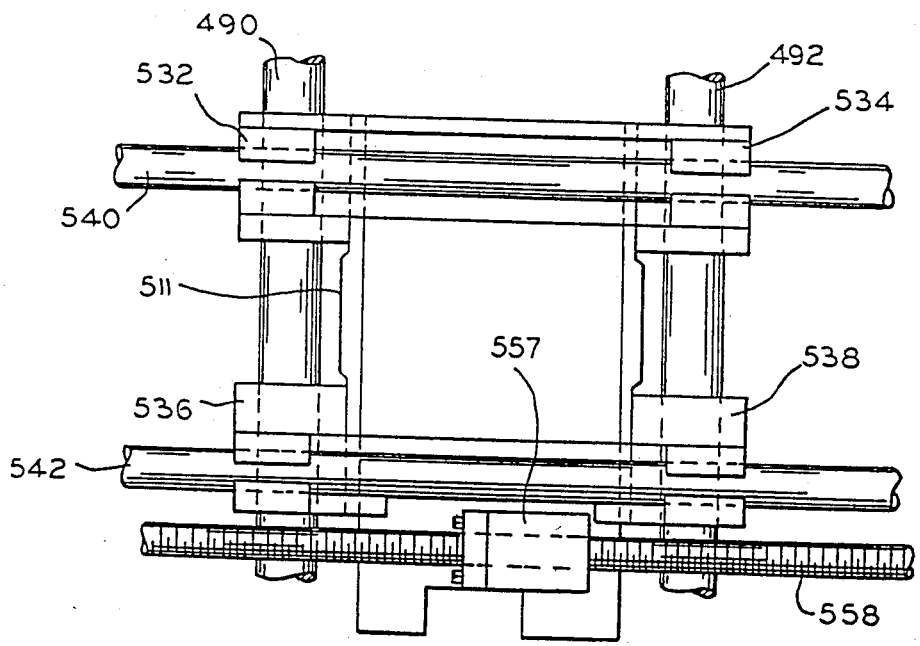
FIG. 14 is a view of the structure in FIG. 2, showing the reverse longitudinal carriage and the carriage drive screw and nut.

Referring now to FIGS. 26, 13, 14, and 27, detector vertical carriage 432 comprises plates 474 and 476 joined together rigidly and rigidly supporting end caps 478 and 480. End caps 478 and 480 are fixed to guide rods 490 and 492, which are also kept parallel by a horizontally disposed plate 494. Referring particularly to FIGS. 13 and 14, guide rods 490 and 492 are vertically slidable within linear bearings 496, 498, 500, and 502, the linear bearings being joined together by members 504, 506, 508, and 510 of longitudinal detector carriage 511 to form a rigid assembly. A nut 512 is secured to member 510 and threaded to a lead screw 514. The respective ends of lead screw 514 are pivotally secured to plate 494 and detector vertical carriage 432, and lead screw 514 is driven by a reversible servomotor 516 (see FIG. 29) secured to longitudinal detector carriage 511, as follows. Sheave 518 is secured to the drive shaft of servomotor 516, and drive belt 520 is driven by sheave 518 and drives sheave 522 secured to lead screw 514. A second sheave 524 secured to lead screw 514 drives an endless belt 526 to drive a sheave 528 secured to vertical detector encoder 530 which is also mounted to longitudinal detector carriage 511.

Longitudinal detector carriage 511 is positioned and driven as follows. Referring to FIGS. 11, 12, 13, 14, and 29, longitudinal detector carriage 511 includes horizontally disposed linear bearings 532, 534, 536, and 538 for receiving longitudinal guide rods 540 and 542. Guide rods 540 and 542 are respectively mounted by stand-offs 544, 546 and mounting shoes 548, 550 to a box beam 552 comprising plates 554 and 556 welded or otherwise suitably secured together into a rigid structure. Box beam 552 is secured at its respective ends to transverse members 330 and 332 of table frame 54. A nut 557 is secured to longitudinal detector carriage 511 and threaded on a longitudinal lead screw 558 which has its respective ends pivotally mounted to transverse members 330 and 332 by bearing members 559 and 560 (best seen in FIG. 10). Lead screw 558 has mounted to it sheaves 562 and 564, the former driving a drive belt 566 connected to a sheave 568 on an encoder 570 mounted by a bracket 571 to transverse member 332. Sheave 564 is driven by a drive belt 572 driven by sheave 574 connected to drive shaft 576 of a reversible servomotor 578 secured to transverse member 332. As before, rotation of lead screw 558 advances or retracts nut 557, and thus longitudinal detector carriage 511, longitudinally of table frame 54.

The foregoing mechanism permits the detector housing 70 to be moved transversely by operating servomotor 442, its transverse position being transmitted by encoder 466; the detector housing can be moved toward or away from the patient support surface 62 (vertically when the table is disposed horizontally) by operating servomotor 516, the vertical position of the detector housing being transmitted by encoder 530; and the detector housing 70 can be moved longitudinally by operating servomotor 578, the longitudinal position of the detector being transmitted by encoder 570. Just as for the source carriages, the position of the desired detector can be optimized by analyzing the encoder signals to determine its present position, formulating a desired position, calculating a correction to obtain the desired position, comparing the proposed correction to interference data stored in memory, instructing the servomotors to make the indicated correction (assuming no interference is found), and confirming the correction by again analyzing the encoder signals.

Now the means for connecting table frame 54 to base 52 and the parts of base 52 will be described. These parts cooperate to allow the table frame 54 to be raised, lowered, or pivoted about a horizontal transverse axis defined by pivot shaft 56. (The structure described immediately below is shown in FIGS. 2, 22 through 25, and 29.)

Pivot shaft 56, secured rigidly with respect to table frame 54 and rotatably received by base 52, is carried within a housing 600 by bearings 602 and 604. The end 606 of pivot shaft 56 (FIG. 23) is keyed to a pinion gear 608, permitting the latter to rotate about the transverse pivot axis of the table. Pinion gear 608 meshes with first and second racks 610 and 612 which are secured to pistons 614 and 616 and linear bearing means 618 and 620. The respective pistons and linear bearing means are received within cylinders 622, 624, 626, and 628, each mounted rigidly on a frame member 630 secured to housing 600. The respective pistons and linear bearings are slidable within the respective cylinders, and the pistons maintain a substantial seal against the interior walls of the cylinders.

Figure 23:
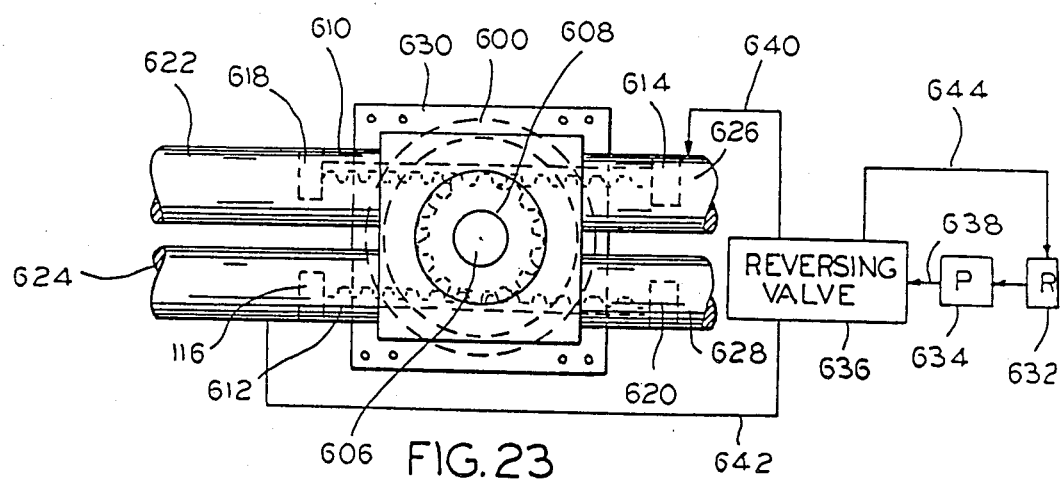
FIG. 23 is a vertical and longitudinal sectional view taken along line 23—23 of FIG. 22, showing the hydraulic drive for tilting the table frame about its transverse pivot axis.
Figure 22:
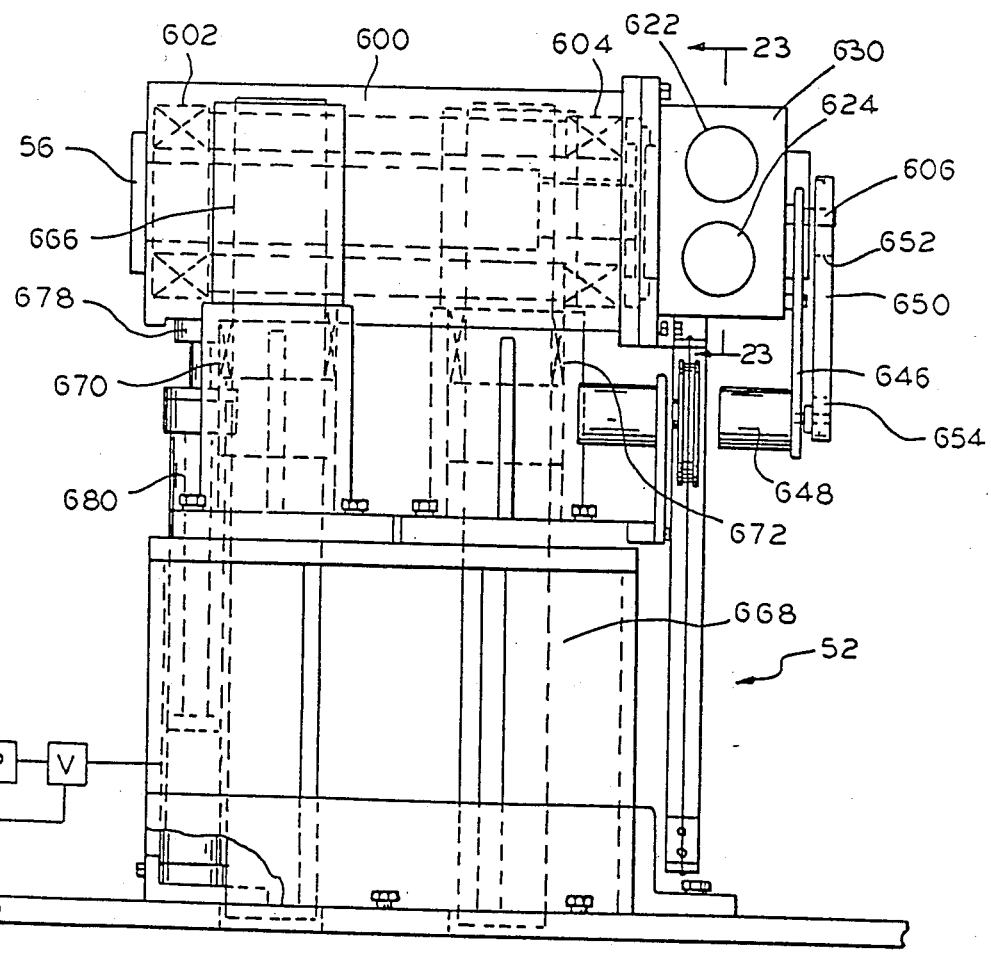
FIG. 22 is a side elevational view, partly in section, of the base of the table assembly shown in FIG. 2.
Figure 25:
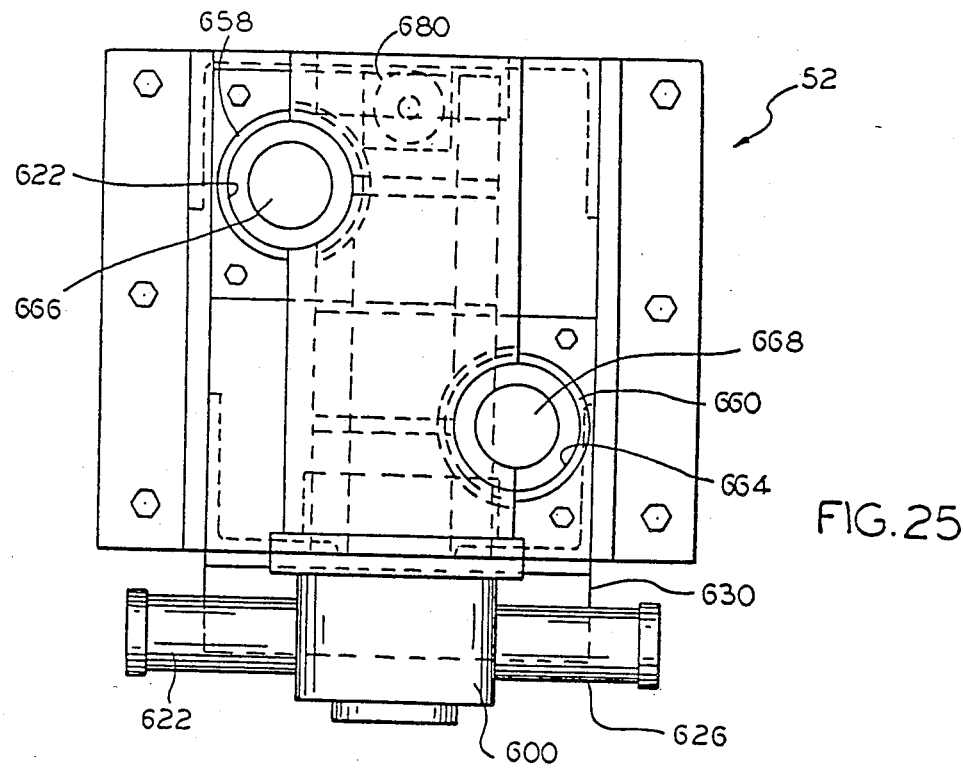
FIG. 25 is a top plan view of the pedestal of the base.
Figure 24:
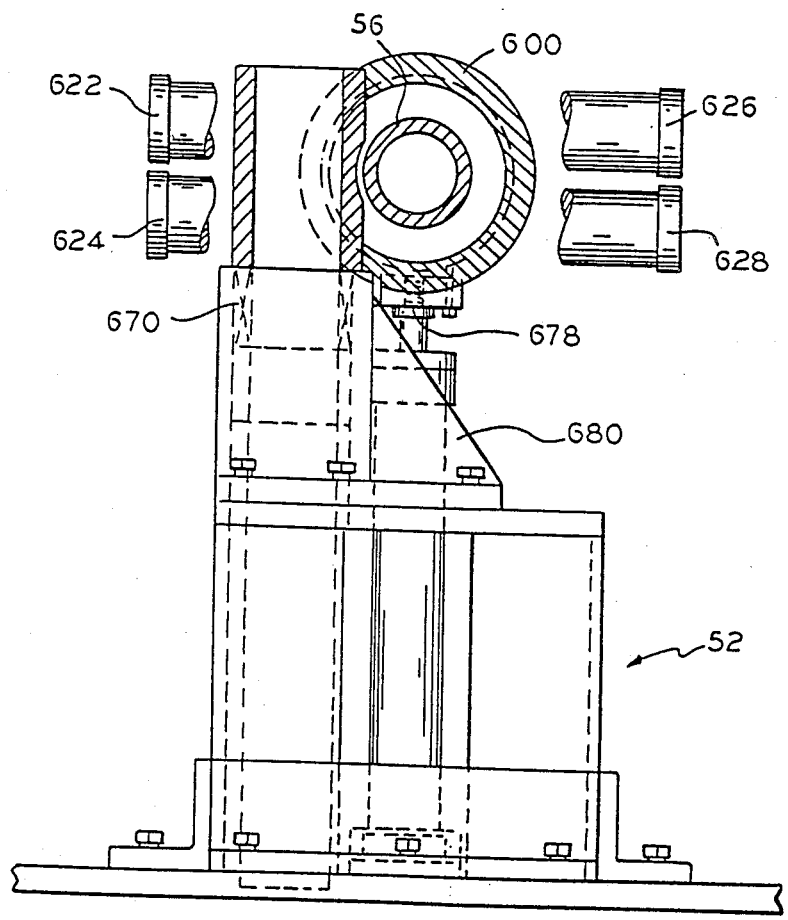
FIG. 24 is a vertical and longitudinal sectional view taken along line 24—24 of FIG. 2, showing the hydraulic means for raising and lowering the transverse pivot axis to raise or lower the table frame.

FIG. 23 schematically illustrates hydraulic means comprising a reservoir 632, a pump 634, a reversing valve 636, and conduits 638, 640 and 642. Reversing valve 636 has one position connecting conduit 638 via conduit 640 with the interior of cylinder 626 to drive piston 614 and to connect the interior of cylinder 624 via conduit 642 with conduit 644 for returning used hydraulic fluid to reservoir 632. When reversing valve 636 is shifted to the opposite position, conduits 640 and 644 are in communication and conduits 642 and 638 are in communication, thereby drawing fluid from cylinder 626 and pumping fluid into cylinder 624. The former position of reversing valve 636 causes pinion gear 608 and table frame 54 to be rotated counterclockwise, while the latter position of valve 636 causes pinion gear 608 and table frame 54 to rotate clockwise. This hydraulic rack and pinion rotation mechanism has the advantage that, if the flow rate of hydraulic fluid is constant, the rate of rotation will be constant throughout the range of rotation.

Housing 600 has cast in ears 658 and 660, respectively having vertically disposed bores 662 and 664 fixed to moving guide rods 666 and 668 received within vertically disposed linear bearings 670 and 672. Bearings 670, 672 are secured by a cast rigid support 674 to pedestal 676 to allow housing 600 to be accurately guided for vertical travel with respect to pedestal 676. Such travel can be effected by moving ram 678 vertically up or down using conventional hydraulic cylinder means 680. In this embodiment of the invention, there is no encoder for travel of housing 600 with respect to pedestal 676 because such information is not critical to positioning the table or translating or pivoting the table, X-ray source, or X-ray detector.

I claim:

1. An X-ray table assembly, comprising:
    a base;
    a table frame supported by said base for titling about a horizontal and transverse pivot axis, said table frame including a patient support surface;
    X-ray source means supported by said table assembly below said patient support surface and including drive means for translating said source means longitudinally and transversely with respect to said patient support surface;
    X-ray detection means supported by said table assembly above said patient support surface and including drive means for translating said detection means longitudinally and transversely with respect to said patient support surface independently of said longitudinal and transverse translation of said X-ray source means; and
    drive means for translating said X-ray detection means toward or away from said patient support surface.

2. The table assembly of claim 1, further comprising linear tomography program means for translating said detection means longitudinally of said patient support while pivoting said X-ray source about said source axis and translating said X-ray source means longitudinally of said patient support, to keep said X-ray source means aimed at said X-ray detection means and through an isocenter adjacent said patient support surface.

3. The invention of claim 1, wherein said X-ray detection means comprises plural detection devices carried on a single subframe for being translated together.

4. The table assembly of claim 3, wherein said plural detection means comprise an electronic image intensifier and an X-ray film holder.

5. The table assembly of claim 4, wherein said X-ray detection means further comprise a spot film holder.

6. An X-ray table assembly, comprising:
a base;
a table frame supported by said base for tilting about a horizontal and transverse pivot axis, said table frame including a patient support surface;
X-ray source means supported by said table assembly on one side of said patient support surface and including drive means for translating said source means longitudinally and transversely with respect to said patient support surface;
X-ray detection means supported by said table assembly on the other side of said patient support surface and including drive means for being translated longitudinally and transversely with respect to said patient support surface;
said drive means for translating said X-ray source means comprising a first lead screw drive for translating said X-ray source means longitudinally, a second lead screw drive for translating said X-ray source means transversely, and a third lead screw drive for translating said X-ray source means toward or away from said patient support surface; and
said drive means for translating said X-ray detection means comprising a first lead screw drive for translating said detection means longitudinally, a second lead screw drive for translating said detection means transversely, and a third lead screw drive for translating said detection means toward or away from said patient support surface.

7. An X-ray table assembly, comprising:
a base,
a table frame supported by said base for tilting about a horizontal and transverse pivot axis, said table frame including a patient support surface;
X-ray source means supported by said table assembly on one side of said patient support surface and including drive means for being translated longitudinally and transversely with respect to said patient support surface; and
X-ray detection means supported by said table assembly on the other side of said patient support surface and including drive means for being translated longitudinally and transversely with respect to said patient support surface;
wherein said pivot axis includes means for being translated vertically with respect to said base, thereby raising or lowering said patient support surface, X-ray source means, and X-ray detection means with respect to said base.

8. An X-ray table assembly comprising:
a base;
a table frame supported by said base for tilting about a horizontal and transverse pivot axis, said table frame including a patient support surface;
X-ray source means supported by said table assembly on one side of said patient support surface and including drive means for translating said source means longitudinally and transversely with respect to said patient support surface;
X-ray detection means supported by said table assembly on the other side of said patient support surface and including drive means for being translated longitudinally and transversely with respect to said patient support surface;
drive means for translating said X-ray source means toward or away from said patient support surface; and
drive means for translating said X-ray detection means toward and away from said patient support surface.

9. The table assembly of claim 8, wherein said drive means for translating said X-ray source means comprise a first lead screw drive for translating said X-ray source means longitudinally, a second lead screw drive for translating said X-ray source means transversely, and a third lead screw drive for translating said X-ray source means toward or away from said patient support surface.

10. The X-ray table assembly according to claim 8 wherein said drive means for said X-ray source means is constructed and arranged for driving said source means independently of said X-ray detection means, and
said drive means for said X-ray detection means is construction and arranged for driving said detection means independently of said X-ray source means.

11. An X-ray table assembly comprising:
a base;
a table frame supported by said base for tilting about a horizontal and transverse pivot axis, said table frame including a patient support surface;
X-ray source means supported by said table assembly on one side of said patient support surface and including drive means for being translated longitudinally and transversely with respect to said patient support surface;
X-ray detection means supported by said table assembly on the other side of said patient support surface and including drive means for being translated longitudinally and transversely with respect to said patient support surface; and
mechanically independent drive means for translating said pivot axis vertically with respect to said base, for tilting said table frame about said pivot axis, for translating said X-ray source means toward or away from said patient support surface, and for translating said X-ray detection means toward or away from said patient support.

12. The table assembly according to claim 11, wherein each drive for said table frame, X-ray source means, and X-ray detection means includes positon encoding means for detecting the relative position and orientation of each said portion of the assembly.

13. The table assembly of claim 11, wherein said drive means for tilting said table frame is hydraulically operated.

14. The table assembly of claim 13, wherein said means for tilting said table frame comprises a hydraulically driven rack slidably supported by said base and a pinion gear coaxial with said pivot axis, fixed with respect to said table frame, and meshed with said rack.

15. The table assembly of claim 14, further comprising a second hydraulically driven rack slidably supported on said base and meshed with said spur gear.

* * * * *